(12) United States Patent
Cook et al.

(10) Patent No.: US 9,040,569 B2
(45) Date of Patent: May 26, 2015

(54) COMPOSITIONS AND METHODS FOR TREATING OR PREVENTING PNEUMOVIRUS INFECTION AND ASSOCIATED DISEASES

(71) Applicant: MICRODOSE THERAPEUTX, INC., Monmouth Junction, NJ (US)

(72) Inventors: Robert O. Cook, Hillsborough, NJ (US); Eugene R. Reynolds, Scotch Plains, NJ (US); Boris Shekunov, Hillsborough, NJ (US); Siead I. Zegar, Orland Park, IL (US)

(73) Assignee: MICRODOSE THERAPEUTX, Monmouth Junction, NJ (US)

( * ) Notice: Subject to any disclaimer, the term of this patent is extended or adjusted under 35 U.S.C. 154(b) by 0 days.

(21) Appl. No.: 13/931,201

(22) Filed: Jun. 28, 2013

(65) Prior Publication Data

US 2014/0005239 A1    Jan. 2, 2014

Related U.S. Application Data

(60) Provisional application No. 61/666,258, filed on Jun. 29, 2012.

(51) Int. Cl.
*C07D 257/04* (2006.01)
(52) U.S. Cl.
CPC .................................. *C07D 257/04* (2013.01)

(58) Field of Classification Search
None
See application file for complete search history.

(56) References Cited

U.S. PATENT DOCUMENTS

| 6,495,580 | B1 | 12/2002 | Nitz et al. |
| 2005/0288344 | A1 | 12/2005 | Nitz et al. |
| 2005/0288345 | A1 | 12/2005 | Rys et al. |

FOREIGN PATENT DOCUMENTS

| WO | WO 02/059132 A1 | 8/2002 |
| WO | WO 2004/014316 A2 | 2/2004 |
| WO | WO 2004/014317 A2 | 2/2004 |

OTHER PUBLICATIONS

Douglas, et al.; *Inhibition of Respiratory Syncytial Virus Fusion by the Small Molecule VP-14637 Via Specific Interactions With F Protein*; Journal of Virology, May 2003; pp. 5054-5064; vol. 77 No. 9.
Morton, et al.; *Structural Characterization of Respiratory Syncytial Virus Fusion Inhibitor Escape Mutants: Homology Model of the F Protein and a Syncytium Formation Assay*; Virology 311 (2003) pp. 275-288.

*Primary Examiner* — Alicia L Otton
(74) *Attorney, Agent, or Firm* — RatnerPrestia

(57) ABSTRACT

The present invention provides novel crystalline polymorphic forms of MDT-637, in particular, crystalline polymorphic forms with physicochemical properties specifically suited for drug production, amorphous formation, composite form, and methods of preparation thereof. The novel polymorphs described herein are useful for the treatment of respiratory disease, such as disease caused by respiratory syncytial virus.

15 Claims, 29 Drawing Sheets

TABLE 17

Figure 1:
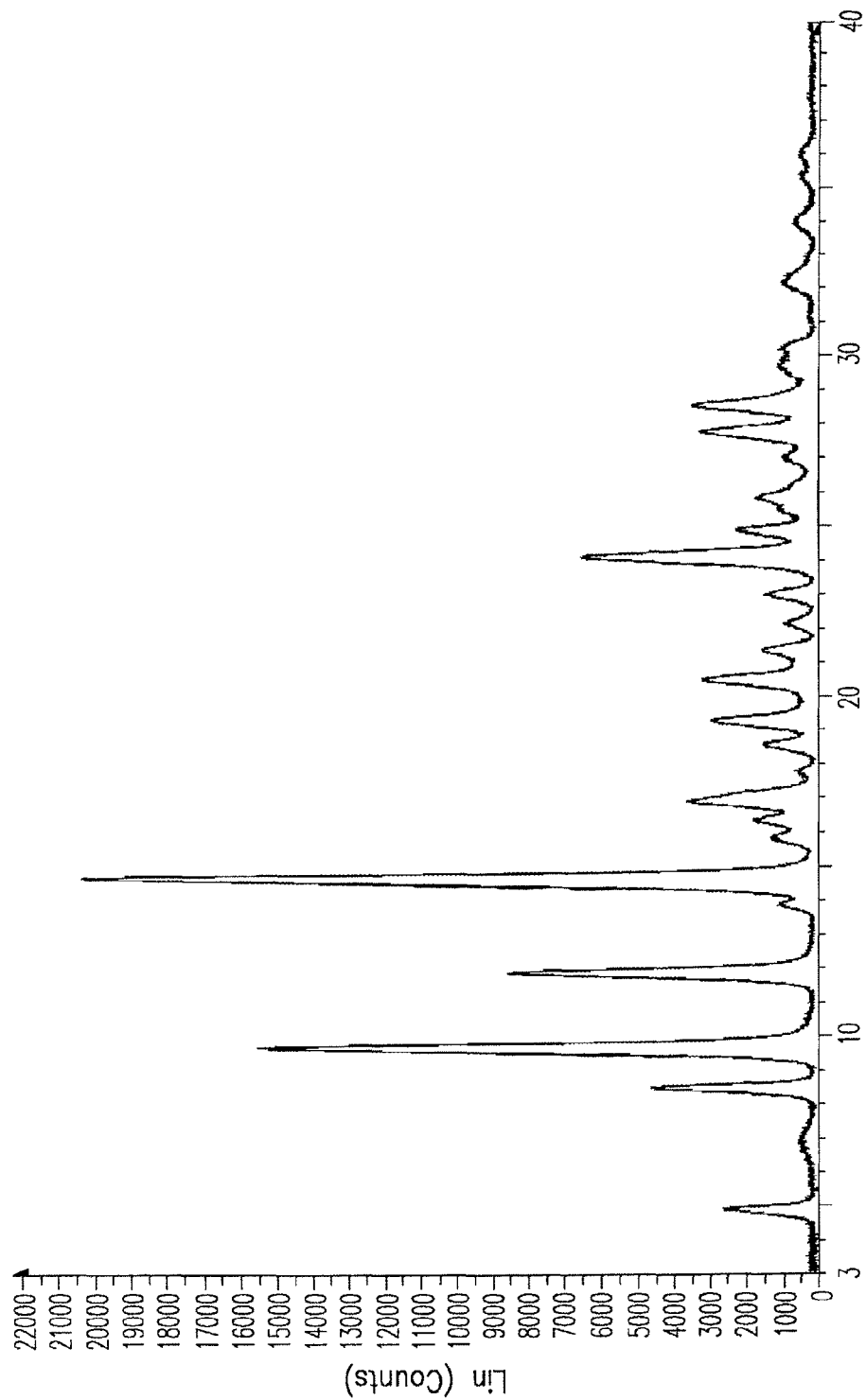

| Major Inclusion Criteria |
| --- |
| 1. Males and/or surgically sterile or post-menopausal females (confirmed by FSH test); males must agree to practice barrier contraception until they are discharged from the study<br>2. Willing to give written informed consent<br>3. 18 to 50 years of age<br>4. BMI of 19-30kg/m2<br>5. Non-smoker (for at least 90 days prior to screening) and willing to abstain from smoking during the course of the study<br>6. Good general health as determined by medical history, physical examination, ECG and clinical laboratory tests<br>7. Willing to abstain from alcohol, caffeine, and xanthine-containing beverages for 24 hours prior to and 24 hours after dosing |

| Major Exclusion Criteria |
| --- |
| 1. Uncontrolled, clinically significant disease which in the opinion of the Principle Investigator and MDT would place the subject at risk through study participation or would confound the assessment of the safety of MDT-637<br>2. Evidence of current or history of respiratory disease, including asthma, emphysema, chronic bronchitis, or cystic fibrosis<br>3. History of significant nasal irritation from nasal inhalation of medication<br>4. History of malignancy<br>5. History of clinically significant alcohol or drug abuse<br>6. Positive drug screen for drugs of abuse<br>7. Positive test for HIV, Hepatitis B or Hepatitis C<br>8. Allergy to lactose, or lactose intolerance<br>9. Use of prescription medication within 14 days of Visit 2 or over-the-counter preparations, including dietary and herbal supplements, within 5 days of Visit 2<br>10. Positive urine pregnancy test at Visit 1<br>11. Inability to perform 3 acceptable, repeatable spirometry maneuvers<br>12. Abnormal FEV1, FVC, or FEV1/FVC (FEV1 or FVC < 90% of predicted and/or FEV1/FVC ratio < 0.75)<br>13. FEV 1 variability > 5% between V1 and V2<br>14. Abnormal QTc interval at Visit 1(> 450msec in males or > 470msec in females)<br>15. Significant blood donation (or testing) in previous 8 weeks<br>16. Use of any Investigational Product in previous 3 months or use of any biotech products (for example: vaccines, antibodies etc) in previous 12 months |

FIG. 27

TABLE 18

| Major Inclusion Criteria |
| --- |
| 1. Males and/or surgically sterile or post-menopausal females (confirmed by FSH test); males must agree to practice barrier contraception until they are discharged from the study
2. Willing to give written informed consent
3. 18 to 50 years of age
4. BMI of 19-30kg/m2
5. Non-smoker (for at least 90 days prior to screening) and willing to abstain from smoking during the course of the study
6. Good general health as determined by medical history, physical examination, spirometry, ECG and clinical laboratory tests
7. Willing to abstain from alcohol, caffeine, and xanthine-containing beverages for 24 hours prior to and 24 hours after dosing |
| Major Exclusion Criteria |
| 1. Uncontrolled, clinically significant disease which in the opinion of the Principle Investigator and Sponsor (MDTx) would place the subject at risk through study participation or would confound the assessment of the safety of MDT-637
2. Evidence of current or history of respiratory disease; for instance asthma, emphysema, chronic bronchitis, or cystic fibrosis
3. Upper respiratory tract infection within 6 weeks of Visit 1
4. Symptoms of rhinitis (stuffy nose, rhinorrhea, sneezing, nasal discharge) within 2wks of Visit 1
5. Current symptoms of cough, dyspnea, wheezing or nocturnal awakenings due to respiratory symptoms
6. History of significant nasal irritation from nasal inhalation of medication
7. History of malignancy
8. History of clinically significant alcohol or drug abuse
9. Positive drug screen for drugs of abuse
10. Positive test for HIV, Hepatitis B or Hepatitis C
11. Allergy to lactose, or lactose intolerance
12. Use of prescription medication within 14 days of Visit 2 or over-the-counter preparations, including dietary and herbal supplements, within 5 days of Visit 2
13. Positive urine pregnancy test at Visit 1
14. Inability to perform reproducible spirometry in accordance with American Thoracic Society/European Respiratory Society (ATS/ERS) guidelines
15. Abnormal FEV1, FVC, or FEV1/FVC (FEV1 < 90% and/or FVC < 90% of predicted and/or FEV1/FVC ratio < 0.75)
16. FEV1 variability > 5% between Visit 1 and Visit 2
17. Abnormal QTc interval at Visit 1(>450msec in males or > 470msec in females)
18. Significant blood donation (or testing) in previous 8 weeks
19. Use of any Investigational Product in previous 3 months (small molecule products) or previous 12 months (biotech products) |

FIG. 28

TABLE 19

| Major Inclusion Criteria |
|---|
| 1. Documented clinical history and physician diagnosis of intermittent or mild or moderate persistent asthma for at least 6 months prior to screening OR subjects with historical record of agonist reversibility within previous 5 years
2. Subjects must demonstrate after administration of an inhaled Beta adrenergic agonist an improvement in FEV1 of 12% or greater, with an absolute change of at least 200ml, from the baseline level, confirming reversibility OR bronchial hyper-reactivity on methacholine challenge with a PC20 less than or equal to 8mg/mL
3. Visit 2 FEV1 (with no treatment change in the interim) must be within 12% of Visit 1 result
4. Males and/or females (if not surgically sterile or confirmed to be post menopausal) must agree to practice 2 barrier contraception until they are discharged from the study
5. Willing to give written informed consent
6. 18 to 50 years of age
7. BMI of 19-30kg/m2
8. Non-smoker (for at least 90 days prior to screening) and willing to abstain from smoking during the course of the study
9. Good general health (excepting asthma) as determined by medical history, physical examination, ECG and clinical laboratory tests
10. Willing to abstain from alcohol, caffeine, and xanthine-containing beverages for 24 hours prior to dosing and for 24 hours after dosing |

| Major Exclusion Criteria |
|---|
| 1. Uncontrolled, clinically significant disease which in the opinion of Principal Investigator, Medical Monitor or Sponsor (MicroDose Therapeutx; MDTx) would place the subject at risk through study participation or would confound the assessment of the safety of MDT-637
2. Inability to perform acceptable and repeatable spirometry in accordance with American Thoracic Society/European Respiratory Society (ATS/ERS) guidelines
3. Abnormal FEV1, FVC, or FEV1/FVC (FEV1 and FVC < 75% of predicted and/or FEV1/FVC ratio < 0.6)
4. FEV1 variability > 12% between Visit 1 and Visit 2
5. Evidence of current or history of additional respiratory disease (other than asthma); for instance emphysema, chronic bronchitis or cystic fibrosis
6. Upper respiratory tract infection within 6 weeks of Visit 1
7. Use of rescue albuterol or other short acting bronchodilator (SAB) more often than five times per week
8. History of significant nasal irritation from nasal inhalation of medication
9. History of malignancy
10. History of clinically significant alcohol or drug abuse
11. Positive drug screen for drugs of abuse
12. Positive test for HIV, Hepatitis B or Hepatitis C
13. Allergy to lactose, or lactose intolerance
14. Use of prescription medication (other than oral contraceptives or SAB and/or low dose inhaled corticosteroid e.g. fluticasone propionate 44mcg BID or budesonide 100mcg BID or equivalent) within 14 days of Visit 2 or over-the-counter preparations, including dietary and herbal supplements, within 5 days of Visit 2
15. Positive urine pregnancy test at Visit 1 or Visit 2 or visit 4
16. Abnormal QTc interval at Visit 1(>450msec in males or >470msec in females)
17. Significant blood donation (or testing) in previous 8 weeks
18. Use of any Investigational Product in previous 6 weeks (small molecule products) or previous 3 months (biological products) |

FIG. 29

COMPOSITIONS AND METHODS FOR TREATING OR PREVENTING PNEUMOVIRUS INFECTION AND ASSOCIATED DISEASES

CROSS REFERENCE TO RELATED APPLICATION

The present application claims priority from U.S. Provisional Application Ser. No. 61/666,258 filed Jun. 29, 2012 the contents of which are incorporated herein in their entirety, by reference.

FIELD OF THE INVENTION

The present invention relates to compounds, compositions and methods for preventing and treating viral infections, and the diseases associated therewith, particularly those viral infections and diseases caused by viruses of the order Paramyxoviridae, including Paramyxovirinae and Pneumovirinae subfamilies. More specifically, the present invention relates to novel crystalline polymorphic forms of MDT-637, in particular, crystalline polymorphic forms with physicochemical properties advantageous for drug product, amorphous form, composite form, and methods of preparation thereof.

BACKGROUND OF THE INVENTION

MDT-637 is an active pharmaceutical ingredient (API) (chemical name: phenol, 2,2'-[(4-hydroxyphenyl)methylene]bis[4-[[(5-methyl-1H-tetrazol-1-yl)imino]methyl]]; alternate name: 5,5'-Bis[1-(((5-methyl-1-H-tetrazolyl)imino)methyl)]-2,2',4''-methylidyne trisphenol; molecular formula $C_{25}H_{22}N_{10}O_3$) as described by the following structure:

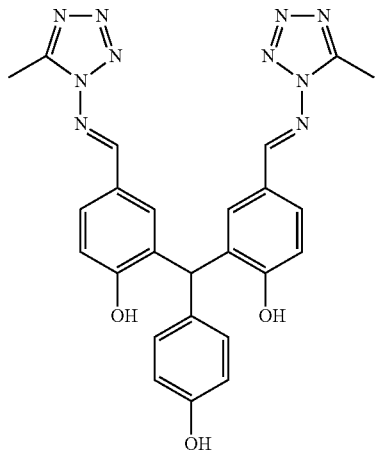

MDT-637 exhibits an antiviral therapeutic activity as described in U.S. Pat. No. 6,495,580 which is hereby incorporated by reference. In addition, U.S. patent application Ser. No. 10/524,162 and U.S. patent application Ser. No. 10/524,313 describe related compounds and compositions and are also incorporated by reference. MDT-637 is associated with preventing and treating viral infections, and the diseases associated therewith, particularly those viral infections and diseases caused by viruses of the order Paramyxoviridae, including Paramyxovirinae and Pneumovirinae subfamilies.

A number of important human diseases are caused by Paramyxoviruses, including mumps, measles, and respiratory syncytial virus (RSV), which is a major cause of bronchiolitis and pneumonia in infants and children both in the US and worldwide. The mechanism of action of MDT-637 has been elucidated in some detail, and though not wishing to be bound by the following theory, it is thought that MDT-637 acts by targeting and blocking the viral fusion protein, which is a target for RSV treatments. In addition to being highly potent (40,000 times more potent than ribavirin) MDT-637 also showed that it was effective in reducing RSV viral count both pre- and post-infection.

The family Paramyxoviridae is composed of a diverse group of viruses and is divided into two subfamilies, Paramyxovirinae and Pneumovirinae.

The major human viruses of the Paramyxoviridae family are: measles virus, mumps virus, the parainfluenza viruses (types 1, 2, 3, 4a, and 4b), and respiratory syncytial virus (RSV). All of the viruses of the Paramyxoviridae family are spread through the respiratory route and are highly contagious. A number of important human diseases are caused by paramyxoviruses. These include mumps, measles, which caused 745,000 deaths in 2001 and respiratory syncytial virus (RSV), which is a major cause of bronchiolitis and pneumonia in infants and children both in the US and worldwide.

Paramyxoviruses are also responsible for a range of diseases in other animal species, for example canine distemper virus (dogs), phocine distemper virus (seals), cetacean morbillivirus (dolphins and porpoises) Newcastle disease virus (birds), and rinderpest virus (cattle). Some paramyxoviruses such as the henipaviruses are zoonotic pathogens, occurring naturally in an animal host, but also able to infect humans. Also included are certain "unassigned" viruses, such as Atlantic salmon paramyxovirus, Beilong virus, J virus, Pacific salmon paramyxovirus, and Tailam virus.

The parainfluenza viruses are the second most common causes of respiratory tract disease in infants and children. They can cause pneumonia, bronchitis and croup in children and the elderly. Infection with parainfluenza viruses typically produce minor upper respiratory tract infections which are characterized by coryza, pharyngitis, low fever, and bronchitis. Parainfluenza viruses are also the most common cause of croup, or laryngotracheobronchitis, in children aged 6 months to 5 years.

Human RSV, the prototypic member of the pneumovirus group, is the major pediatric viral respiratory tract pathogen, causing pneumonia and bronchiolitis in infants and young children. According to the US National Institutes of Health, human RSV infection, the single most important cause of severe respiratory illness in infants and young children and the major cause of infantile bronchiolitis, is the most frequent cause of hospitalization of infants and young children in industrialized countries. In the USA alone, from 85,000 to 144,000 infants with RSV infection are hospitalized annually, resulting in 20%-25% of pneumonia cases and up to 70% of bronchiolitis cases in the hospital. Global RSV disease burden is estimated at 64 million cases and 160,000 deaths every year.

Children who experience RSV infection early in life run a high risk of subsequent recurrent wheezing and asthma, especially premature infants and infants with bronchopulmonary dysplasia, for whom preventive passive immunization with anti-RSV monoclonal antibodies such as Palivizumab is highly recommended. RSV also is a significant problem in the elderly, in persons with cardiopulmonary diseases and in immunocompromized individuals. RSV attack rates in nursing homes in the USA are approximately 5%-10% per year with a 2%-8% case fatality rate, amounting to approximately 10,000 deaths per year among persons older than 64 years of age.

Attempts to develop vaccines for RSV are ongoing, but none have yet been demonstrated to be safe and efficacious. Vaccine development has been shadowed by adverse reactions exhibited by the initial formalin-inactivated RSV vaccine introduced in the late 1960s. Immunized children showed an increased incidence of RSV lower respiratory tract disease and developed abnormally severe illnesses, including death. Chemotherapy with ribavirin [1-beta-D-ribofuranosyl-1H-1,2,4-triazole-3-carboxamide], an antiviral nucleoside which is the only pharmaceutical approved by the U.S. Food and Drug Administration (FDA) for treatment of RSV disease, is considered only for certain RSV patients (e.g., those at high risk for severe complications or who are seriously ill with this infection). However, its efficacy and value are controversial. Recent studies have reported a failure to demonstrate either clinical or economic benefit to patients of ribavirin treatment. Moreover, ribavirin has certain toxic side-effects and, in order to minimize these, strict administrative procedures in a closed environment must be followed.

A human intravenous immune globulin (IVIG) preparation is licensed for prophylactic use in certain patients at high-risk for RSV disease. Administration of this drug requires intravenous infusion of a large volume over a 2 to 4 hour period in children who have limited venous access due to prior intensive therapy, as well as compromised cardiopulmonary function. Moreover, intravenous infusion necessitates monthly hospital visits during the RSV season, which in turn places children at risk of nosocomial infections.

None of the above-described regimens satisfies the need for effective vaccines or therapeutics for RSV infection. Given the high risk of occurrence, along with the high incidence of mortality amongst vulnerable populations (pediatric, immunocompromised, elderly), there is a clear need for novel and effective therapeutic regimens that can alleviate and eliminate the complications associated with pneumovirus infections.

As described above, there is a wide array of infections associated with Paramyxovirinae and Pneumovirinae pathogens, and accordingly, it is evident that there exists a need for improved therapeutic regimens that can alleviate and eliminate complications associated with infection. Currently, no such therapeutics are available. In particular, a need exists for new anti-viral agents and treatments for RSV infection that overcome the shortcomings of existing pharmaceutical preparations.

MDT-637 is recognized as an effective antiviral compound, but there continues to be a need for improved compositions having desirable therapeutic characteristics such as modes of delivery and optimized distribution allowing effective and safe dosing. In addition, there is a need for compositions with beneficial physical and chemical properties, stability and handling characteristics. Furthermore, there is need for novel and consistently predictable methods of manufacturing, thereby reducing the potential for heterogeneous compositions.

SUMMARY OF THE INVENTION

The present invention provides an improvement over prior art vaccines and therapeutics by providing novel compositions for the treatment and prevention of infection caused by, or associated with, Paramyxovirinae and Pneumovirinae infection. In particular, the novel compositions and methods of the present invention are well suited to therapeutic intervention in infection caused by the major viruses of the Paramyxoviridae family including, but not limited to, measles virus, mumps virus, the parainfluenza viruses (types 1, 2, 3, 4a, and 4b), and respiratory syncytial virus (RSV). The improved compositions and methods of the present invention satisfy the heretofore unmet need in the art for therapeutic intervention that enables the alleviation of symptoms such as rhinitis, otitis media, pneumonia and bronchiolitis. In addition, the novel compositions and methods of the present invention are particularly desirable due to improved stability, improved solubility, low dosing levels, ease of handling, dosing and administration as well as the significant reduction and absence of side effects and toxicity. Surprisingly, the compositions described herein display unexpected results with regard to therapeutic efficacy.

The methods and compositions described herein are particularly suited for treating Paramyxovirinae and Pneumovirinae infection, however, as would be evident to one skilled in the art, they may also be utilized for additional indications.

The present invention provides new crystal forms of MDT-637 with unique structure, hydration or solvation levels as well as novel methods of their production.

The present invention provides a novel crystal form, denominated as form of pattern MDT-637 P-3 dihydrate (or simply P-3 dihydrate) which is found to be particularly advantageous for drug delivery of MDT-637.

In another aspect, the present invention provides a novel crystal form of P-3 ethanolate which plays an important role in purification and production of P-3 dihydrate.

In another aspect, the present invention provides a novel crystal form of P-3 monohydrate.

In another aspect, the present invention provides a novel crystal form of P-3 anhydrous.

In another aspect, the present invention provides an additional novel MDT-637 P-2 crystal form, denominated as form of pattern P-2 hydrate (or simply P-2 hydrate) which is shown to be the most thermodynamically stable form at ambient conditions.

In another aspect, the present invention provides a novel crystal form, P-2 anhydrous.

In another aspect, the present invention provides a purification recrystallization process for P-2 and P-3 forms resulting in high-purity product with the API content preferably above 98% w/w.

In another aspect, the present invention provides other novel crystal forms, exhibiting PXRD patterns denoted as P-4, P-6, P-7 and P-8 (alternatively MDT-637 P4, MDT-637 P6, MDT-637 P7 and MDT-637 P8).

In another aspect, the present invention provides a novel amorphous form.

In another aspect, the present invention provides a novel solid composite form of API dispersed in a suitable pharmaceutical excipient.

In addition, some novel crystal forms of the present invention are particularly desirable due to their improved solubility and/or solid-state stability, producing low dosing levels, ease of handling and processing, such as micronization, formulation mixing and blister filling, allowing enhanced dosing regimen and administration, lower dosage as well as the significant reduction and absence of side effects and toxicity. The novel crystal forms described herein display unexpected results in terms of their physicochemical and therapeutic properties.

The present invention comprises a pharmaceutical composition comprising a therapeutically effective amount of a crystal form of P-3 dihydrate, or P-3 ethanolate, or P-3 monohydrate, or P-3 anyhydrous, or P-2 anhydrous, P-4, P-6, P-7, P-8, or an amorphous form, or combinations thereof, and at least one pharmaceutically acceptable carrier.

In addition, the crystal forms and synthesis methods described herein are improvements over prior art compositions and methods in that they comprise novel polymorphic forms enabling the production of improved pharmaceutical formulations and dosage forms having enhanced therapeutic value.

Accordingly, it is an object of the present invention to provide disclosure of novel MDT-637 crystal forms and methods of their preparation resulting in pharmaceutical products associated with treatment and prevention of different viral infections, in particular with treatment and prevention viral infections using respiratory drug delivery, wherein such forms and compositions are optimized for ease of delivery, for dosing, for stability and reduced toxicity.

Accordingly, it is an object of the present invention to provide novel compositions and methods for alleviating and preventing symptoms associated with Paramyxovirinae and Pneumovirinae infection.

Another object of the present invention is to provide novel compositions and methods for alleviating and preventing symptoms associated with measles virus, mumps virus, the parainfluenza viruses, and respiratory syncytial virus (RSV).

Another object of the present invention is to provide novel compositions and methods for alleviating and preventing symptoms associated with respiratory syncytial virus (RSV) wherein such symptoms comprise rhinitis, otitis media, pneumonia, bronchiolitis and death.

Yet another object of the present invention is to provide novel compositions and methods for alleviating and preventing symptoms associated with Paramyxovirinae and Pneumovirinae infection wherein such compositions may be delivered in low dosages.

A further object of the present invention is to provide novel compositions and methods for alleviating and preventing symptoms associated with Paramyxovirinae and Pneumovirinae infection wherein such compositions are optimized for ease of delivery, for dosing, for stability and reduced toxicity.

An additional object of the present invention is to provide novel compositions and methods for alleviating and preventing symptoms associated with Paramyxovirinae and Pneumovirinae infection wherein such compositions are optimized for ease of delivery to subjects having limited ability such as infants, elderly, immunocompromised individuals and subjects having restricted inspiratory airflow.

Another object of the present invention is to provide novel compositions and methods for alleviating and preventing symptoms associated with Paramyxovirinae and Pneumovirinae infection wherein such methods facilitate and encourage therapeutic compliance.

Yet another object of the present invention is to provide novel compositions and methods for alleviating and preventing symptoms associated with RSV, wherein such compositions are optimized for ease of delivery to subjects having restricted inspiratory airflow.

Another object of the present invention is to provide novel compositions and methods for alleviating and preventing symptoms associated with respiratory syncytial virus (RSV) wherein such symptoms comprise rhinitis, otitis media, pneumonia, bronchiolitis and death and wherein such compositions are optimized for ease of delivery, for dosing, for stability and reduced toxicity and wherein such compositions comprise compositions and methods comprising unique.

A further object of the present invention is to provide novel compositions and methods comprising unique polymorphic forms of MDT-637 and related compounds.

Another object of the present invention is to provide novel compositions and methods comprising unique polymorphic forms of MDT-637 and related compounds, wherein such compositions comprise the polymorph exhibiting PXRD patterns denoted as P-2, P-3, P-4, P-6, P-7 and P-8.

Another object of the present invention is to provide novel compositions and methods comprising unique polymorphic forms of MDT-637 and related compounds, and pharmaceutically acceptable excipients.

A further object of the present invention is to provide novel compositions and methods comprising unique polymorphic forms of MDT-637 wherein such polymorphic forms are optimized for delivery to a subject via inhalation.

These and other objects, features and advantages of the present invention will become apparent after a review of the following detailed description of the disclosed embodiments and the appended claims.

BRIEF DESCRIPTION OF THE FIGURES

FIG. 1 provides a characteristic PXRD pattern of P-2 hydrate crystal form.

FIG. 2 provides a characteristic PXRD pattern of P-2 anhydrous crystal form.

FIG. 3 provides a characteristic FTIR pattern of P-2 hydrate crystal form.

FIG. 4 provides a characteristic DSC trace of P-2 hydrate crystal form.

FIG. 5 provides a characteristic TGA trace of P-2 hydrate crystal form.

FIG. 6 provides a characteristic DVS absorption/desorption curves for conversion between anhydrous and hydrate crystal forms of pattern P-2.

FIG. 7 provides a flow chart showing an example of crystallization, filtration, drying and hydration processes to produce high-purity P-2 hydrate crystal form.

FIG. 8 provides a characteristic PXRD pattern of P-3 dihydrate crystal form.

FIG. 9 provides a characteristic PXRD pattern of P-3 monohydrate crystal form.

FIG. 10 provides a characteristic PXRD pattern of P-3 anhydrous crystal form.

FIG. 11 provides a characteristic PXRD pattern of P-3 ethanolate crystal form.

FIG. 12 provides a characteristic FTIR pattern of P-3 dihydrate crystal form.

FIG. 13 provides a characteristic DSC trace of P-3 dihydrate crystal form.

FIG. 14 provides a characteristic TGA trace of P-3 dihydrate crystal form.

FIG. 15 provides characteristic DVS absorption/desorption curves for conversion between anhydrous, monohydrate and dihydrate crystal forms of pattern P-3 at temperature 20° C.

FIG. 16 provides a flow chart showing an example of re-crystallization, filtration, drying and hydration processes to produce high-purity P-3 dihydrate crystal form.

FIG. 17 illustrates the thermodynamic relationship (hierarchy) of the P-2 and P-3 families of crystal forms.

FIGS. 18*a* and 18*b* provide graphs depicting solubility of different crystal forms in simulated lung fluid (SLF): P-2, P-3, and mixture of P-3 (approximately 75% w/w) and P-2 (approximately 25% w/w). The data are shown for: (a) non-hydrogenated DPPC (Sigma-Aldrich, USA) and (b) hydrogenated DPPC (Lipoid LLC, USA) surfactants at 0.02% w/v concentration. Each data point represents a triplicate sample obtained at temperature 37° C.

Figure 19:
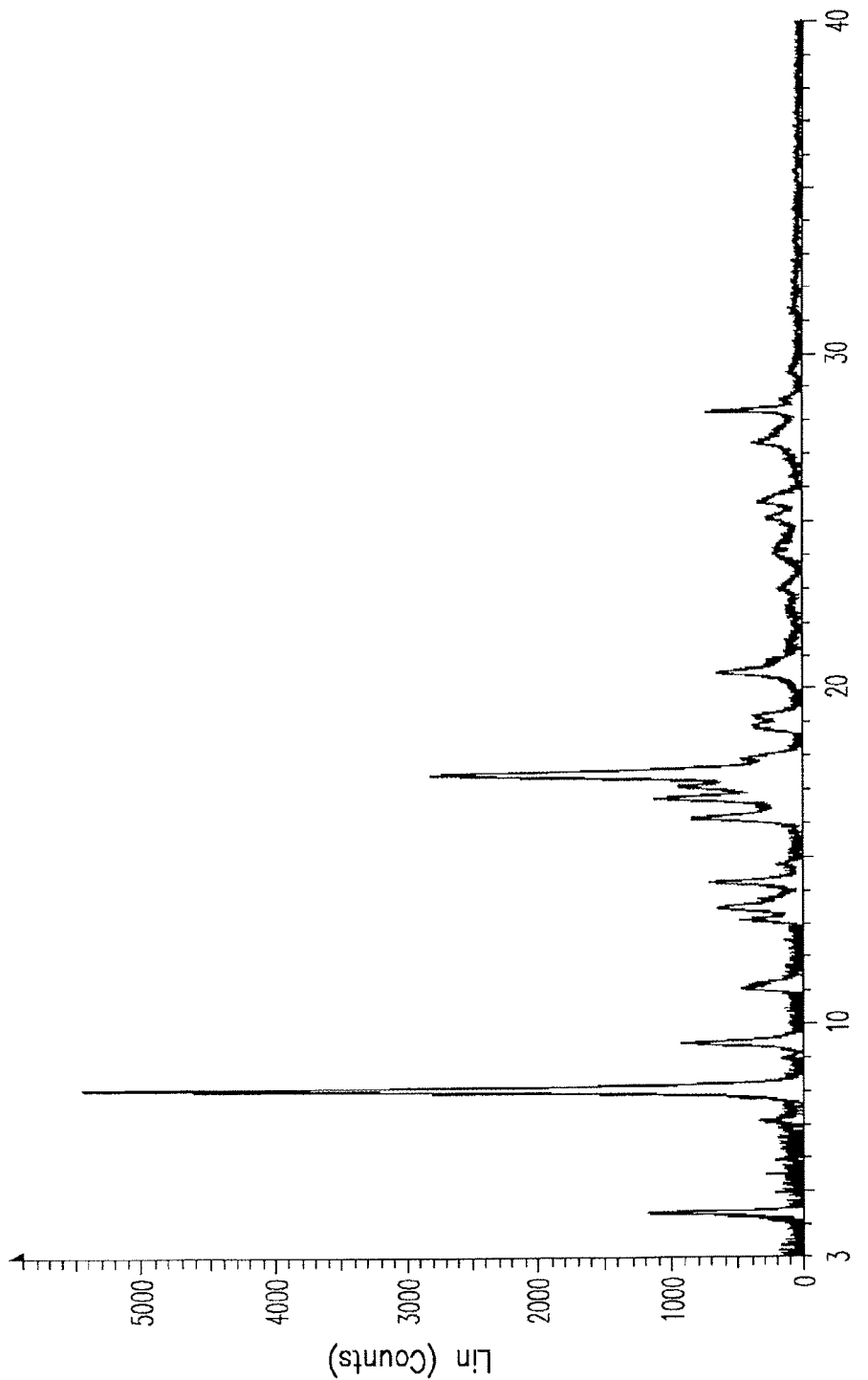

FIG. 19 provides a characteristic PXRD pattern of P-4 crystal form.

Figure 20:
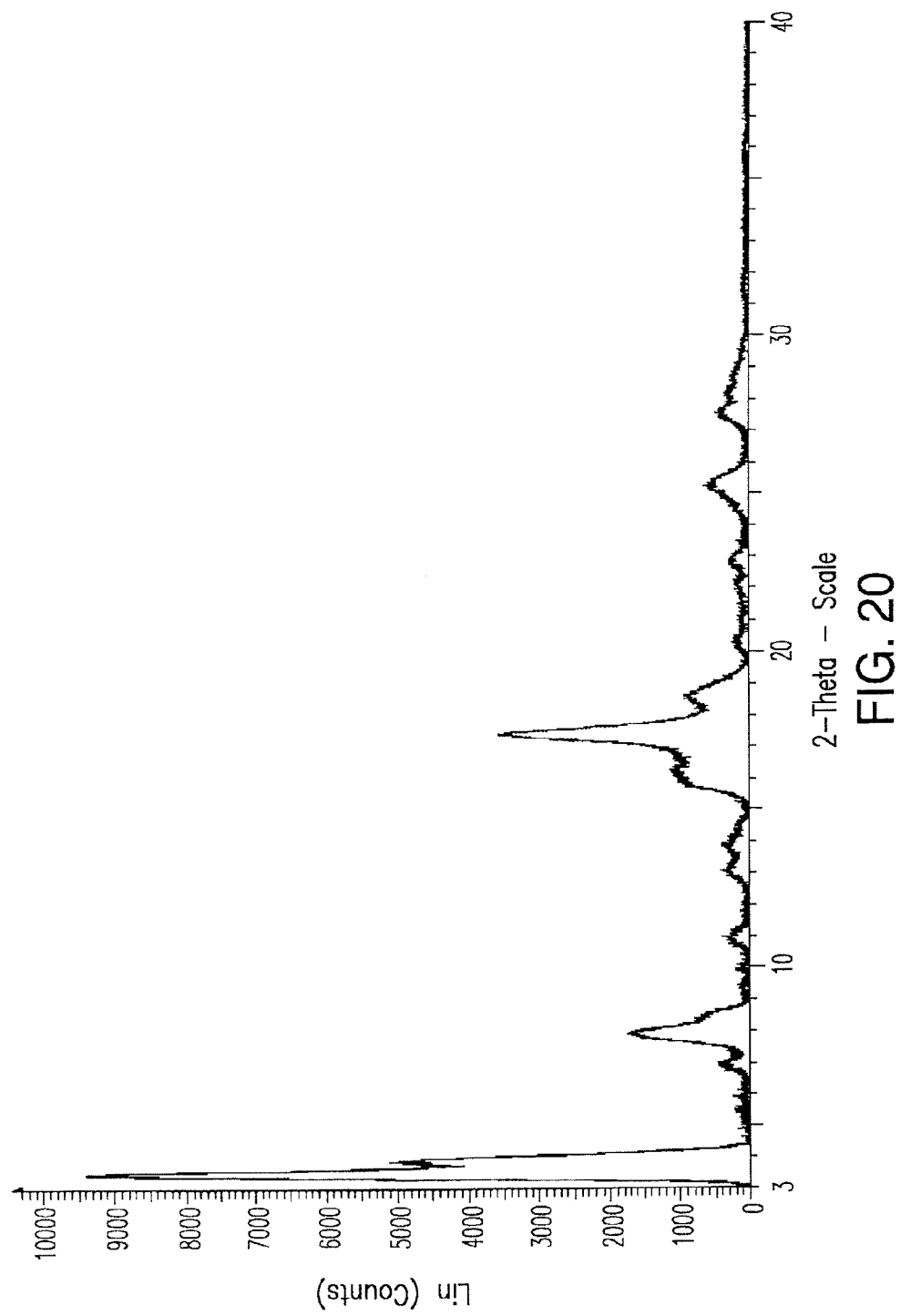

FIG. 20 provides a characteristic PXRD pattern of P-6 crystal form.

Figure 21:
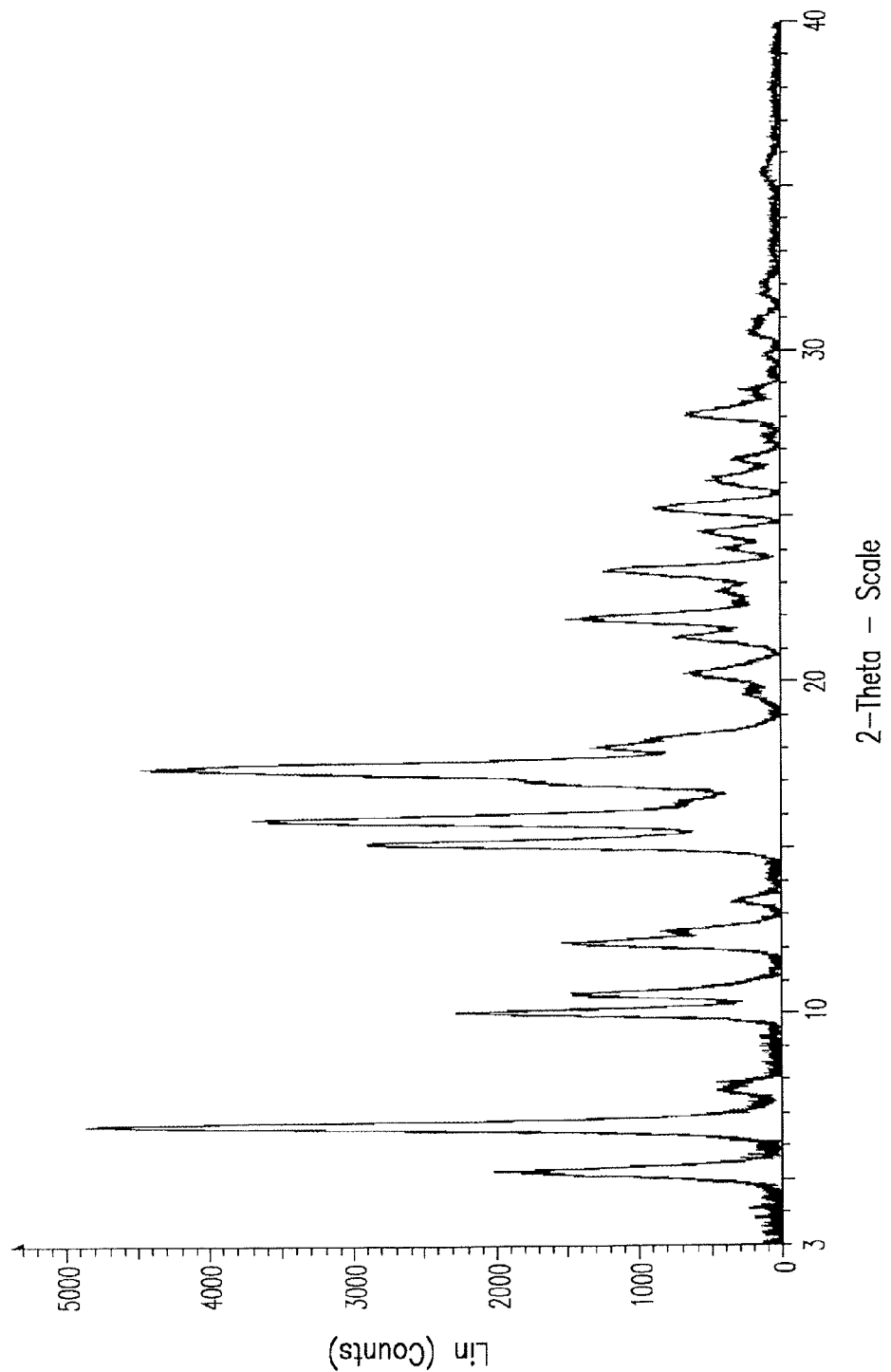

FIG. 21 provides a characteristic PXRD pattern of P-7 crystal form.

Figure 22:
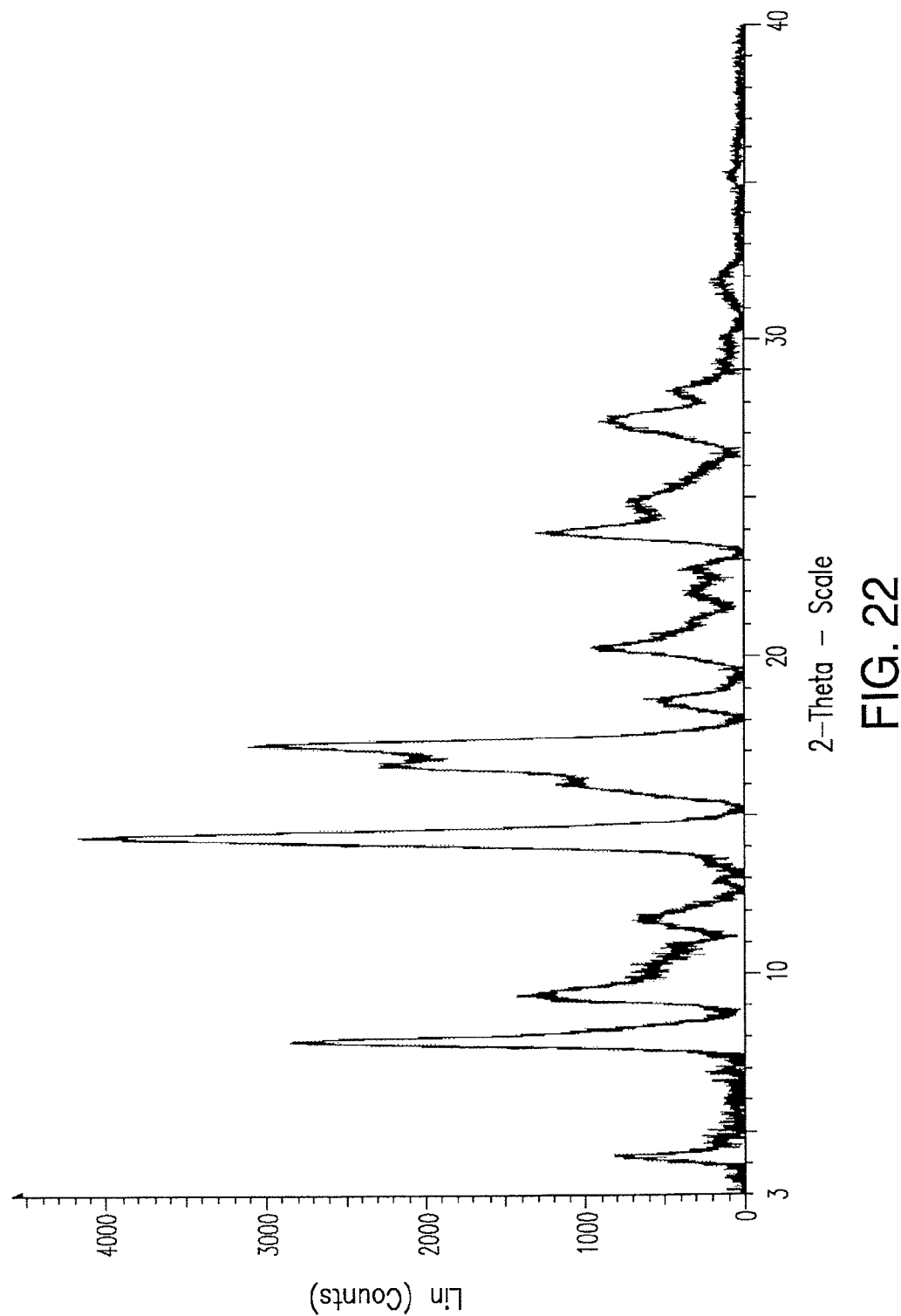

FIG. 22 provides a characteristic PXRD pattern of P-8 crystal form.

Figure 23:
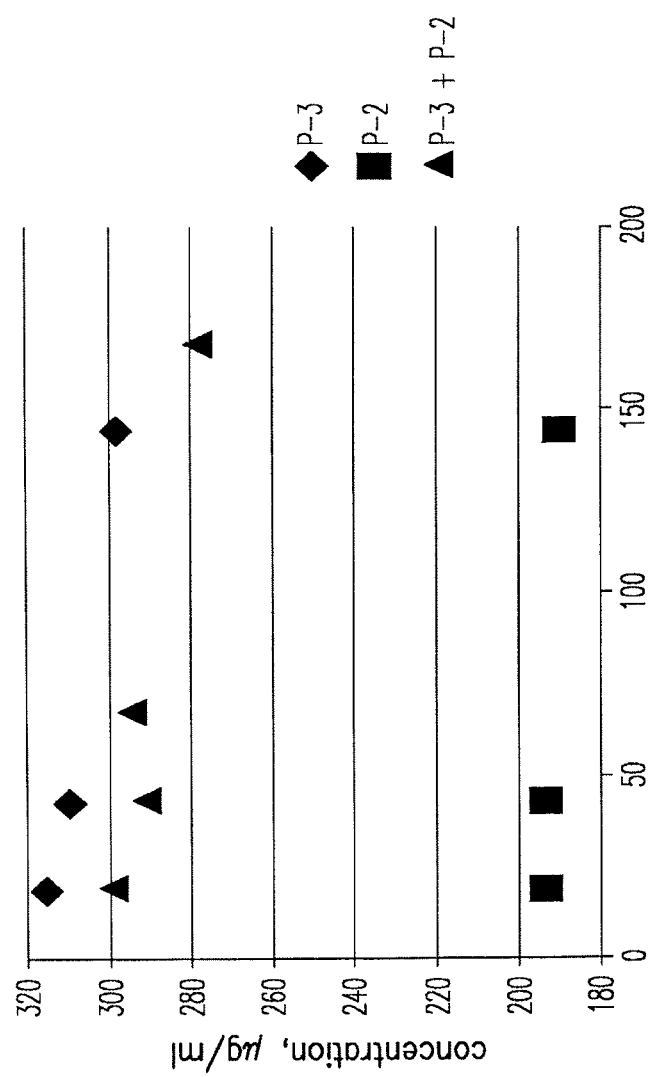

FIG. 23 gives the results of solubility study of drug concentration in stirred suspensions at 25° C. as a function of time for P-2, P-3 forms and their physical mixture in acetonitrile-water 50/50 v/v solution.

Figure 24:
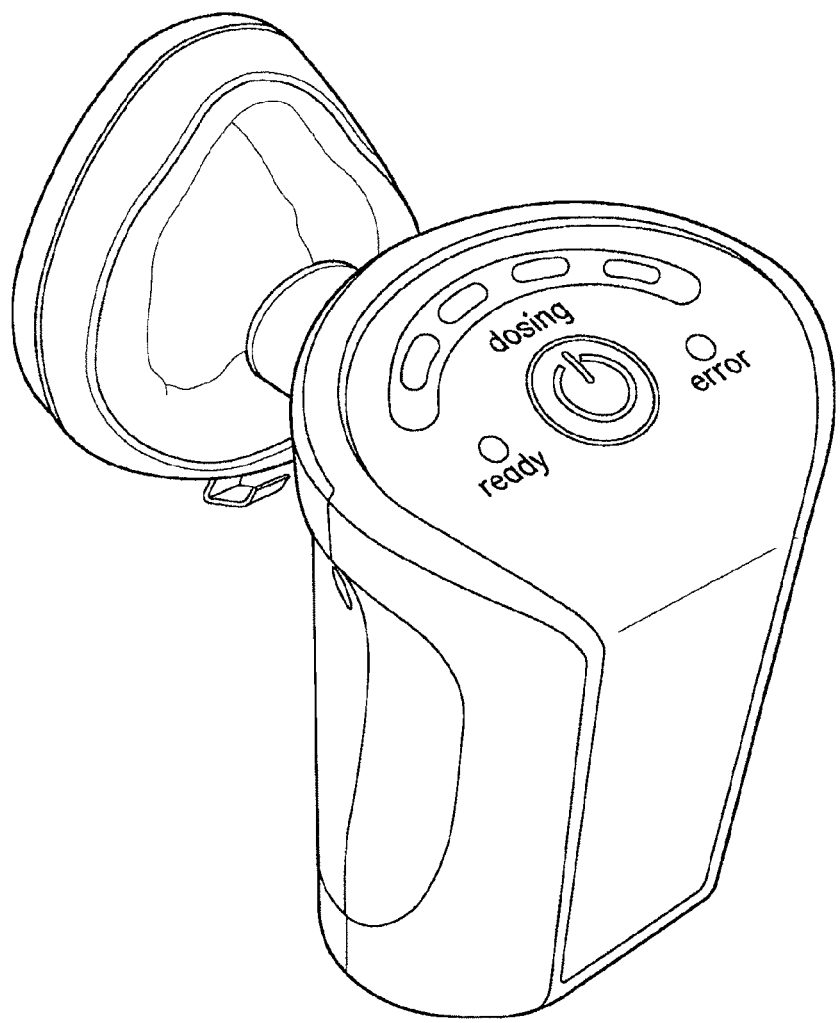

FIG. 24 provides a schematic of an inhaler suitable for use with the present invention and described for example in Example 27.

Figure 25:
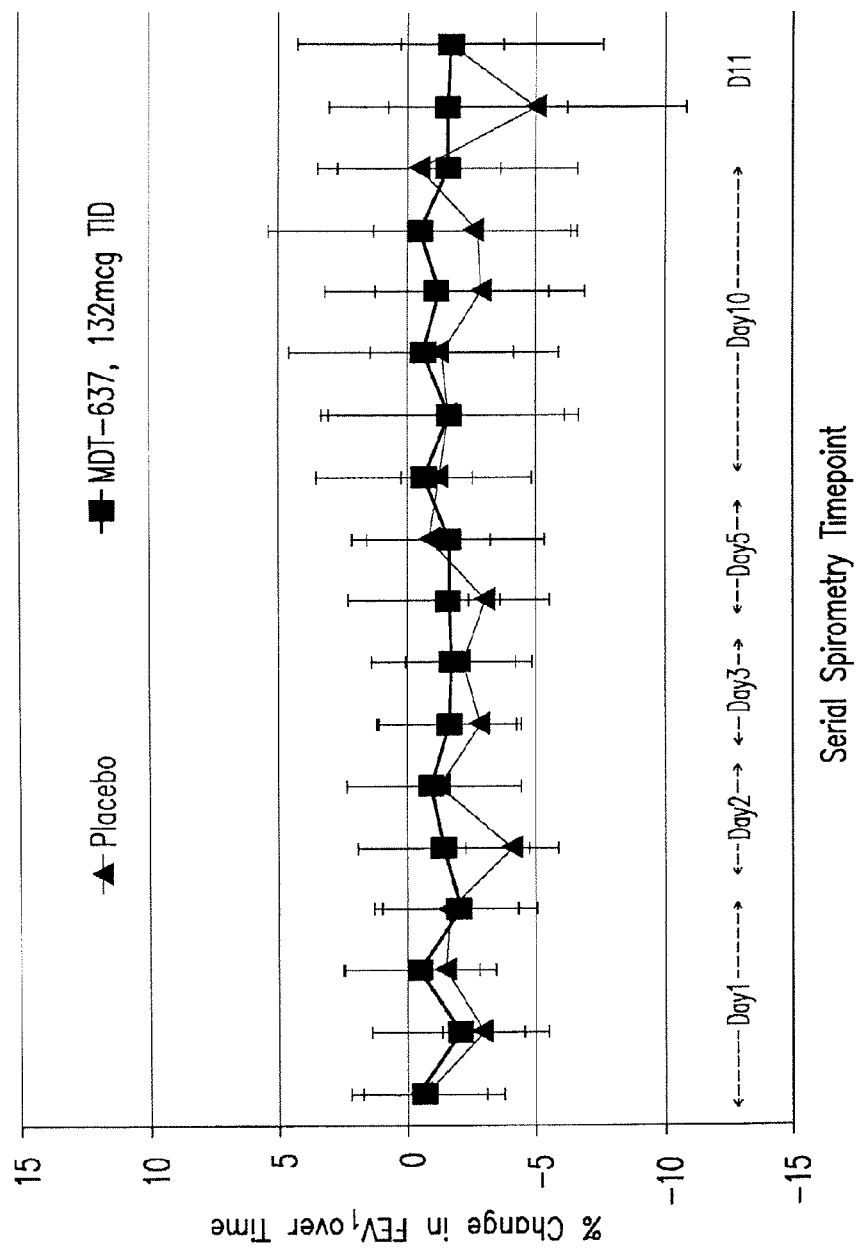

FIG. 25 provides a graph showing serial spirometry for high dose level of MDT-637 P-3 polymorph vs. placebo showing no effect on pulmonary function from inhalation.

Figure 26:
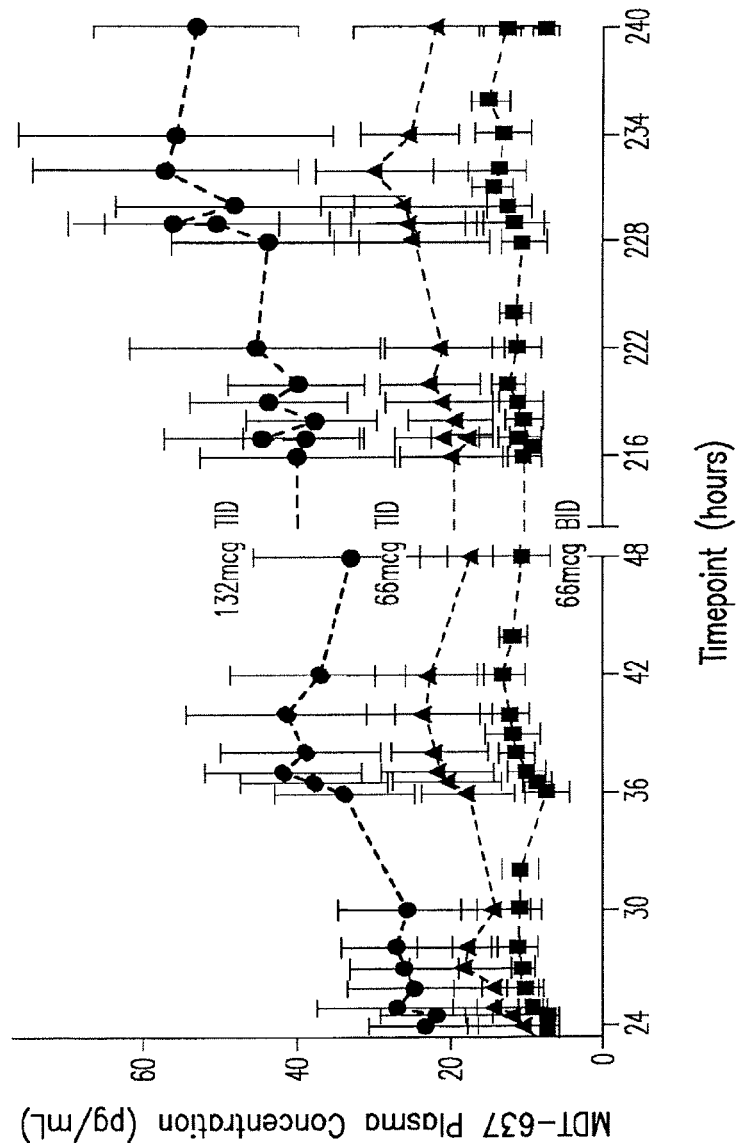

FIG. 26 provides a graph showing limited plasma exposure over 10 days dosing with minimal accumulation between Day 2 and Day 10 across each of 3 dose levels of MDT-637 P-3 polymorph.

FIG. 27 provides TABLE 17 showing the inclusion and exclusion criteria used in selecting patients for Study 1.

FIG. 28 provides TABLE 18 showing the inclusion and exclusion criteria used in selecting patients for Study 1.

FIG. 29 provides TABLE 19 showing the inclusion and exclusion criteria used in selecting patients for Study 1.

DETAILED DESCRIPTION OF THE INVENTION

The present invention may be understood more readily by reference to the following detailed description of the specific embodiments included herein. Reference is made to the accompanying drawings, which form a part hereof, and in which is shown, by way of illustration, various embodiments of the present disclosure. Although the present invention has been described with reference to specific details of certain embodiments thereof, it is not intended that such details should be regarded as limitations upon the scope of the invention.

The entire text of the references mentioned herein are hereby incorporated in their entireties by reference including U.S. Provisional Application Ser. No. 61/666,258 filed Jun. 29, 2012, U.S. Pat. No. 6,495,580 filed on Jan. 29, 1999, U.S. patent application Ser. No. 10/524,162 filed on Aug. 11, 2003 and U.S. patent application Ser. No. 10/524,313 filed on Aug. 11, 2003.

The present invention provides novel polymorphs of the compound MDT-637 described in U.S. Pat. No. 6,495,580 and its structure is shown below. The polymorphs described herein are novel and unobvious in the way that their unique crystalline forms do not follow or result from any prior art and/or theoretical computations/predictions. The polymorphs described herein are produced under specific unobvious crystallization conditions which do not follow from any prior art chemical synthesis production steps or procedures: crystallization from the final synthetic step may result in different forms or mixture of different forms without appropriate controls disclosed herein. An additional point of novelty is that crystal forms discovered have unexpected and unique physiochemical properties such as solubility, dissolution rate, stability, chemical reactivity, hygroscopicity, and powder handling properties which provide advantageous characteristics enabling the production of improved pharmaceutical formulations and dosage forms having enhanced therapeutic value.

Though not wishing to be bound by the following theory, it is believed that MDT-637, its isomers and polymorphs function as fusion inhibitors. For example, in the case of RSV, it is believed that MDT-637, its isomers and polymorphs function as a fusion inhibitor that prevents the attachment of RSV to human cells via F fusion and G attachment glycoproteins.

As used herein, the phrases and terms "active pharmaceutical ingredient", "API", "drug substance" or "drug" refer to MDT-637 compound with the chemical name: phenol, 2,2'-[(4-hydroxyphenyl)methylene]bis[4-[[(5-methyl-1H-tetrazol-1-yl)imino]methyl]]; alternate name: 5,5'-Bis[1-(((5-methyl-1-H-tetrazolyl)imino)methyl)]-2,2',4"-methylidyne trisphenol; molecular formula $C_{25}H_{22}N_{10}O_3$) as described by the following structure:

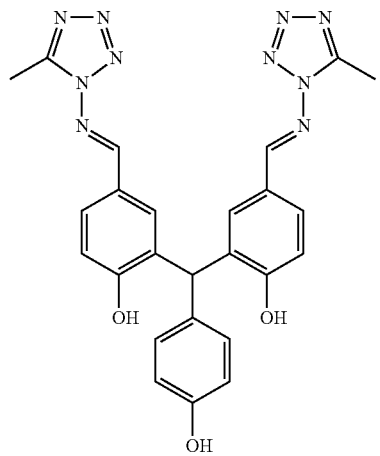

As used herein, the terms "crystal form of pattern P-2, or P-3, or P-4, or P-6, or P-7, or P-8" or "form P-2, or P-3, or P-4, or P-6, or P-7, or P-8" or MDT-637 P2, MDT-637 P3, MDT-637 P4, MDT-637 P6, MDT-637 P7, MDT-637 P8, all refer to the designation of different polymorphs and solvates of the API according to their PXRD patterns, sequentially numbered according to the time of their discovery. Several crystal forms, such as isomorphic solvates, may exhibit a similar PXRD pattern.

As used herein, the terms "Characteristic PXRD pattern" or "characteristic FTIR pattern" means that these patterns exhibit the same positions and sequence of peaks within the limits defined by the analytical methods and instrumentation. Because of the variation between different samples, instruments and natural variability of measurements, the peak positions may deviate from reported positions. In case of the PXRD, this deviation may be as much as 0.2 degrees in 2θ values. There may also be large differences in PXRD peak intensities due to instrument and sample variability, particle size, crystallinity, and the phenomenon of preferential crystal orientation known in the prior art.

As used herein, the terms "characteristic DSC trace" or "characteristic TGA trace" or "characteristic DVS curve" refer to the shape of corresponding dependencies such as the magnitude of variation of the parameter measured as a function of temperature and relative humidity (% RH), as well as to the major inflection points in such dependencies. It is understood in the prior art that these dependences may exhibit significant deviations due to the variation between different samples and measurement technique, in particular, variation in the level of initial sample hydration, the type and scanning speed of the instruments utilized.

As used herein, the term "crystallinity" generally describes imperfections of crystal lattice (a multitude of crystal defects) that can generally be associated with broadening of the PXRD peaks.

As used herein, the term "solid composition" generally refers to the API distributed in a solid matrix of a suitable pharmaceutical excipient, both in a form of molecular dispersion, amorphous dispersion or nanoparticles.

As used herein, the term "water-miscible solvent" generally comprises a solvent that can be mixed in any ratio with drug solution without phase separation.

As used herein, the term "water-immiscible solvent" generally comprises a solvent that can be mixed only partially with drug solution without phase separation.

As used herein, the term "antisolvent" generally comprises a solvent that can be used in crystallization of the drug compound which is miscible with drug solution but in which the drug is practically insoluble.

As used herein, the term "ambient conditions" generally refers to a range of temperatures typically between 15-37° C., and relative humidity between 40-100%.

As used herein, the terms "pharmaceutically acceptable excipients or pharmaceutically acceptable carrier medium" comprise any solid or liquid substances, diluents, dispersion or suspension agents, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the API of the invention, such as by producing any undesirable biological effect or otherwise interacting in a deleterious manner with any other component(s) of the pharmaceutical composition, its use is contemplated to be within the scope of this invention.

Crystal (polymorphic) forms of the same drug substance can be defined as "different crystalline forms of the same pure substance in which the molecules have different arrangements and/or different conformations of the molecules" (Grant, D. J. W., *Theory and Origin of Polymorphism*, in *Polymorphism in Pharmaceutical Solids*, H. G. Brittain, Editor 1999, Marcel Dekker: New York). However the regulatory agencies which control or monitor drug products in different countries, and pharmaceutical industry in general, define solid polymorphism broadly. This definition includes all crystalline forms that contain a drug substance, including solvates with different stoichiometric and non-stoichiometric relationships, as well as salts and amorphous materials (*U.S. Department of Health and Human Services, F.D.A., Center for Drug Evaluation and Research (CDER), ANDAs: Pharmaceutical Solid Polymorphism, Chemistry, Manufacturing, and Controls Information, in Guidance for Industry* 2007). As used herein, "forms" or "polymorphs" or "crystal polymorphic forms" are understood to be different crystalline forms in which the molecules have different arrangements and/or different conformations of the molecules, including forms of a pure substance and all crystalline forms that contain a drug substance, including solvates with different stoichiometric and non-stoichiometric relationships, as well as salts and amorphous materials.

The majority of molecules of synthetic and semi-synthetic origin, which are currently in pharmaceutical development, have high molecular weight and significant conformational mobility. Such molecules may have multiple polymorphic forms and numerous solvates. Crystal polymorphism has a direct effect on several characteristics of both drug substances (active pharmaceutical ingredients, APIs) and solid drug products. For example, polymorphism may affect API physicochemical properties such as melting point, intrinsic density, hardness, hygroscopicity; powder characteristics such as bulk density, flowability, cohesiveness and may also differ in analytical characteristics such as powder X-ray diffraction (PXRD) pattern and/or spectroscopic pattern, measured for example using Fourier-Transform Infra-Red (FTIR) spectroscopy or by Nuclear Magnetic Resonance (NMR) spectroscopy, and thermal behavior as measured using differential scanning calorimetry (DSC) and thermogravimetric analysis (TGA), as well as water sorption/desorption profile as measured using Dynamic Vapor Sorption (DVS) method. Importantly, polymorphism affects the equilibrium solubility and dissolution rates in different solvents (including bodily fluids), and therefore may produce different pharmacokinetic profiles and therapeutic concentrations for the same drug molecule. Unstable or metastable polymorphs may convert into more thermodynamically stable polymorphs during storage or processing. Polymorphs of the same drug molecule may also exhibit different chemical impurities and degradation products after processing and upon storage. Thus different polymorphs may have advantageous and disadvantageous properties for drug products. The structure, properties and methods of preparations of new polymorphs of MDT-637 are subjects of the present invention.

Powder X-ray diffraction (PXRD) analysis was used as the major technique for crystal form identification and performed by the methods known in the art using Bruker D8 Advance Diffractometer with Bragg-Brentano optics. A conventional $CuK$, radiation of wavelength 1.5418 Å was generated with settings of 40 kV and 40 mA throughout all analyses. Samples were mounted onto a silicon low-background holder and flattened with wax paper and a glass slide to form a smooth, thin, uniform sample surface. The data was collected from 3-40° 2θ values in steps of 0.01° 2θ and at a rate of 0.3 seconds/step. Diffraction patterns were processed with Eva 13 software (Bruker AXS GmbH, Karlsruhe, Germany).

As described below, several novel polymorphic forms and solvates of the API were discovered. The materials of patterns P-2 and P-3 show particular utility with regard to stability, solubility and suitability for development of novel pharmaceutical dosage forms. These specific polymorphs are highly relevant to the final API production step and have a high impact on the product manufacturability, e.g., purity, micronization, powder blending, dose filling and formulation performance, including but not limited powder potency, content uniformity and aerosolization efficiency (delivered dose and aerodynamic particle size distribution as measured by a Cascade Impactor (CI), such as Andersen Cascade Impactor (ACI) and New Generation Impactor (NGI) techniques known to those skilled in the art.

The characteristic diffraction peaks of the hydrate crystal form of pattern P-2 are shown in FIG. 1 and listed in TABLE 1. The most characteristic peaks for P-2 hydrate are observed at 2θ values: 4.83°; 8.42°; 9.61°; 11.83°; 14.60°; 16.94°; 19.25°; 20.46°; 24.09°; 24.85°; 27.76°; 28.56°.

TABLE 1

P-2 (Hydrate Crystal Form) Characteristic Diffraction Peaks

| 2Θ, ° | d-value, Å | Relative Intensity % |
|---|---|---|
| 4.83 | 18.30 | 12.50 |
| 6.83 | 12.92 | 2.00 |
| 8.42 | 10.50 | 22.60 |
| 9.61 | 9.19 | 78.70 |
| 11.83 | 7.47 | 43.30 |
| 13.84 | 6.39 | 5.00 |
| 14.60 | 6.06 | 100.00 |
| 15.86 | 5.58 | 5.50 |
| 16.35 | 5.42 | 8.40 |
| 16.94 | 5.23 | 16.80 |
| 17.76 | 4.99 | 2.40 |
| 18.53 | 4.78 | 6.60 |
| 19.25 | 4.61 | 14.30 |
| 20.46 | 4.34 | 15.50 |
| 21.31 | 4.17 | 7.10 |
| 22.13 | 4.01 | 4.00 |
| 22.98 | 3.87 | 6.80 |
| 24.09 | 3.69 | 33.00 |
| 24.85 | 3.58 | 10.60 |
| 25.50 | 3.49 | 5.10 |
| 25.80 | 3.45 | 7.80 |
| 27.00 | 3.30 | 4.30 |
| 27.76 | 3.21 | 15.60 |
| 28.56 | 3.12 | 17.00 |
| 29.71 | 3.00 | 5.20 |
| 30.24 | 2.95 | 4.80 |
| 31.25 | 2.86 | 0.60 |
| 32.24 | 2.77 | 4.30 |
| 33.99 | 2.64 | 2.50 |
| 35.36 | 2.54 | 1.70 |
| 36.01 | 2.49 | 1.90 |

Figure 2:
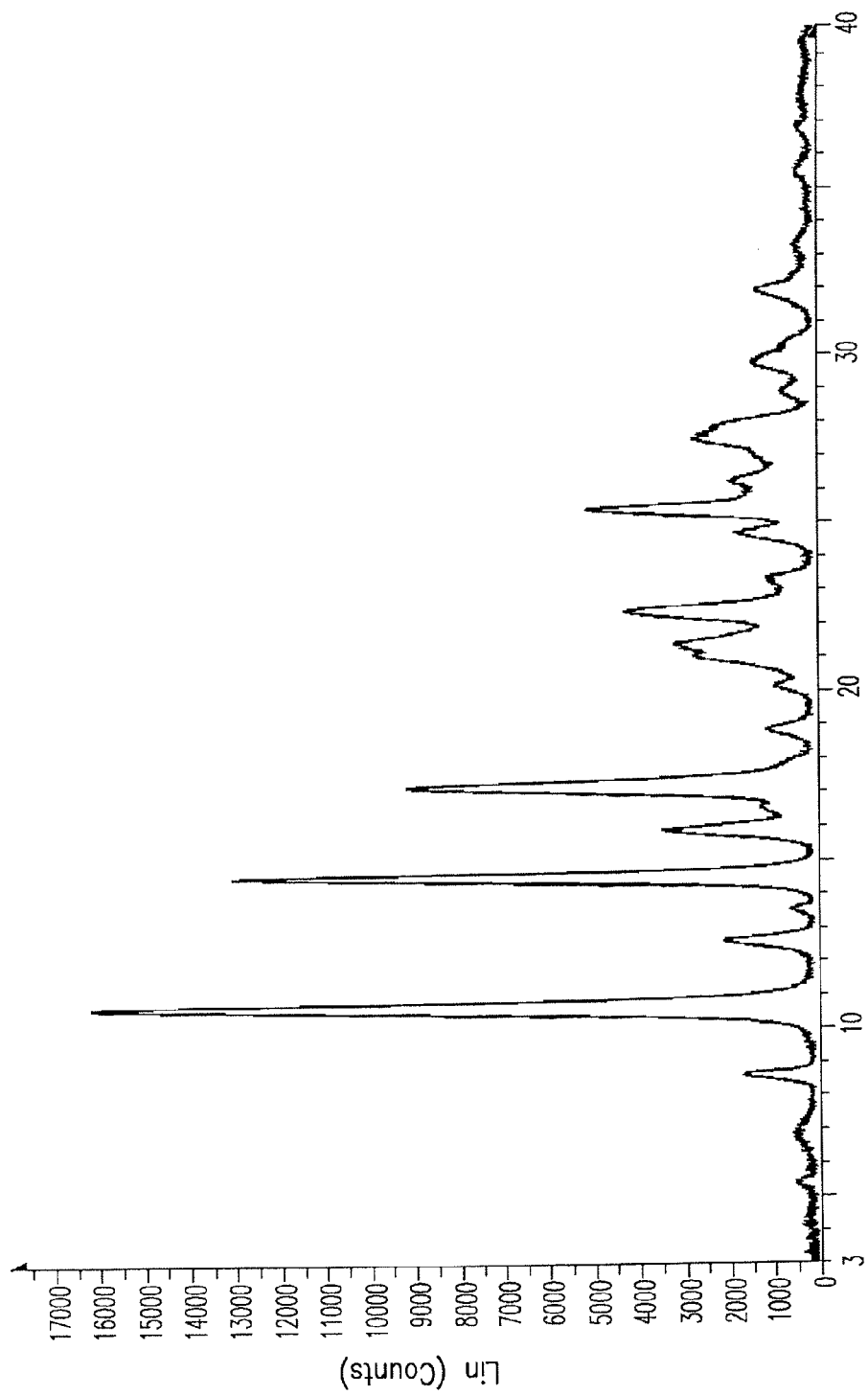

The characteristic diffraction peaks of the anhydrous crystal form of pattern P-2 are shown in FIG. 2 and listed in TABLE 2. The most characteristic peaks for P-2 anhydrous form are observed at 2θ values: 8.58°; 10.64°; 12.58°; 14.51°; 15.89°; 17.20°; 21.06°; 21.41°; 22.37°; 25.43°; 27.62°.

TABLE 2

P-2 (Anhydrous Crystal Form) Characteristic Diffraction Peaks

| 2Θ, ° | d-value, Å | Relative Intensity % |
|---|---|---|
| 5.35 | 16.52 | 2.20 |
| 6.81 | 12.97 | 2.70 |
| 8.58 | 10.30 | 9.50 |
| 10.64 | 8.31 | 100.00 |
| 12.58 | 7.03 | 11.90 |
| 13.52 | 6.54 | 3.00 |
| 14.51 | 6.10 | 79.30 |
| 15.89 | 5.57 | 20.30 |
| 17.20 | 5.15 | 55.50 |
| 18.85 | 4.70 | 6.20 |
| 20.18 | 4.40 | 4.70 |
| 21.06 | 4.22 | 16.50 |
| 21.41 | 4.15 | 19.20 |
| 22.37 | 3.97 | 25.50 |
| 23.26 | 3.82 | 5.60 |
| 24.68 | 3.60 | 10.00 |
| 25.43 | 3.50 | 31.00 |
| 26.22 | 3.40 | 10.60 |
| 27.62 | 3.23 | 15.40 |
| 28.92 | 3.08 | 3.80 |
| 29.82 | 2.99 | 8.10 |
| 31.95 | 2.80 | 7.50 |
| 33.30 | 2.69 | 2.10 |

The PXRD data for P-2 forms obtained under controlled temperature and humidity indicated a pronounced difference between diffraction patterns for hydrated and anhydrous forms of P-2 attributed to lattice expansion and water incorporation. Therefore it is possible to distinguish the hydrated and anhydrous forms of P-2 lattice from the PXRD peak shifts although the lattice does not undergo dramatic structural changes.

Figure 3:
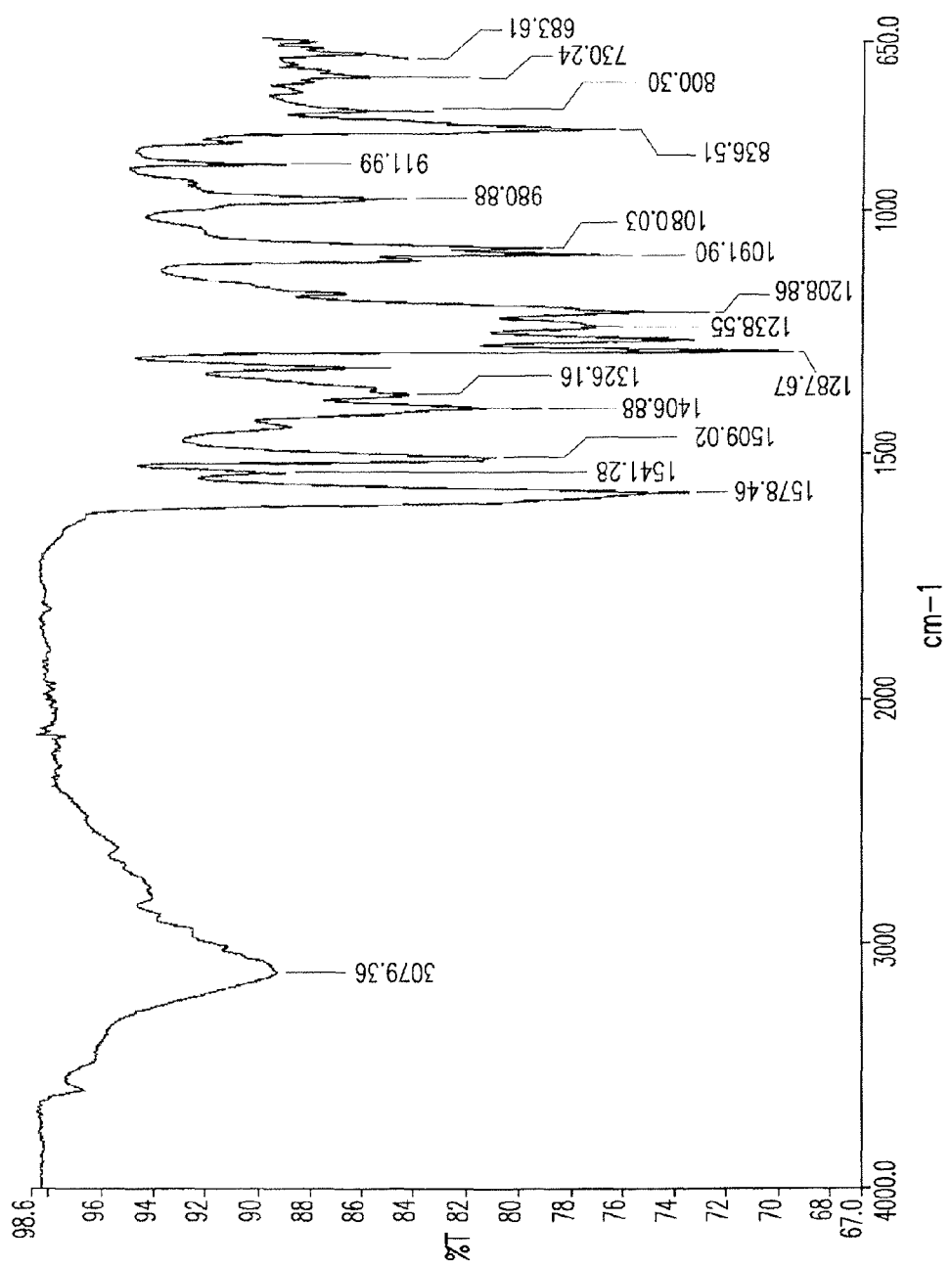

FIG. 3 represents a characteristic FTIR pattern of the P-2 hydrate. The most characteristic absorption bands in the region are between 800-1200 $cm^{-1}$, corresponding to P-2 crystal forms are: 836.5 $cm^{-1}$; 980.9 $cm^{-1}$, double peak at 1080.0 and 1091.9 $cm^{-1}$, 1208.9 $cm^{-1}$, 1238.6 $cm^{-1}$ and 1287.67 $cm^{-1}$.

Figure 4:
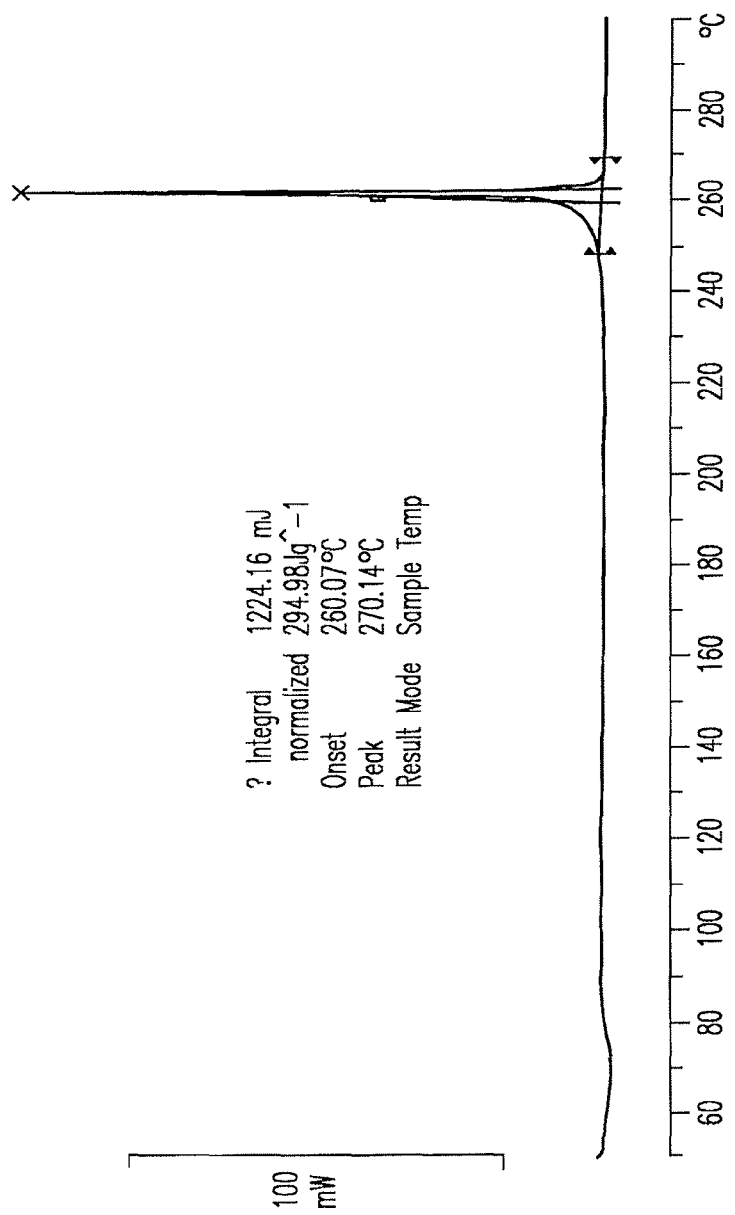
Figure 5:
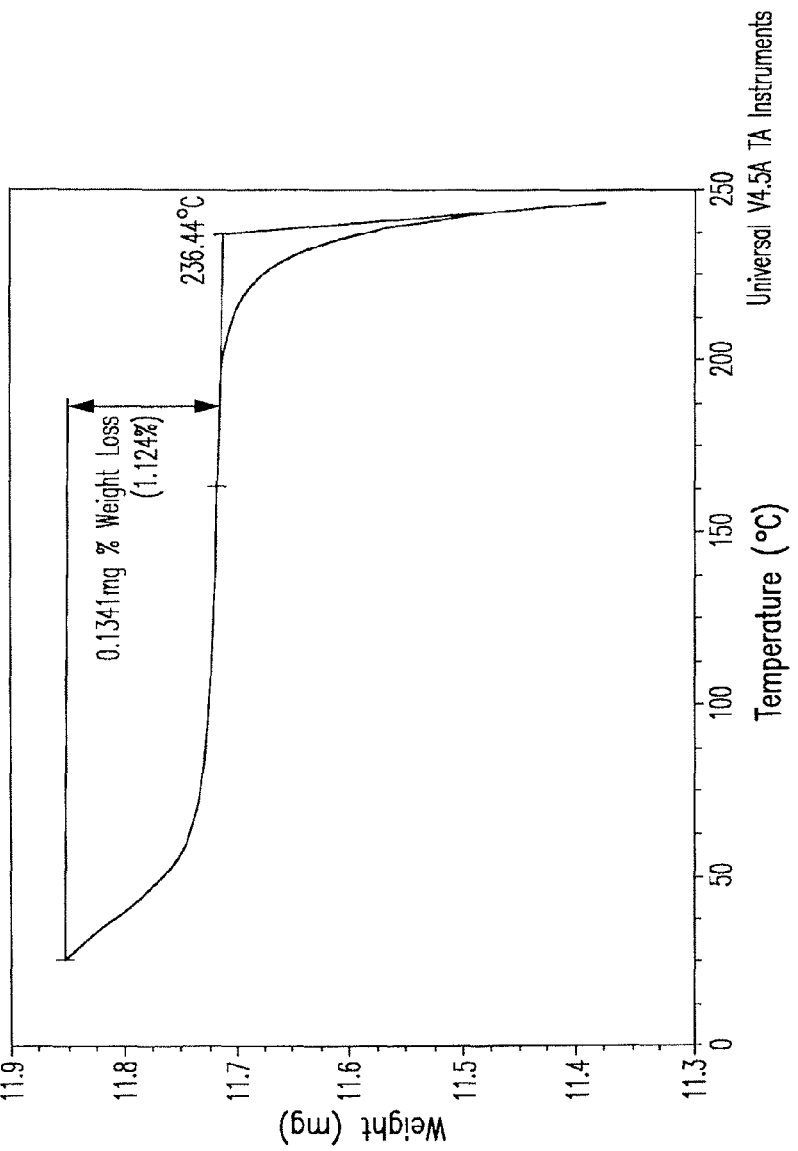

DSC trace for P-2 hydrate (FIG. 4) indicate a sharp melting peak at approximately 263° C., with a small thermal event between 40° C. to 60° C., likely dehydration as confirmed by loss of weight within this temperature interval according to TGA data (FIG. 5). Though not wishing to be bound by any particular theory, it is believed that P-2 loses water relatively easily at temperatures about 60° C., but melts without lattice transition and may constitute a channel hydrate with a stable dehydrate product (stable crystal lattice without further phase transition).

Figure 6:
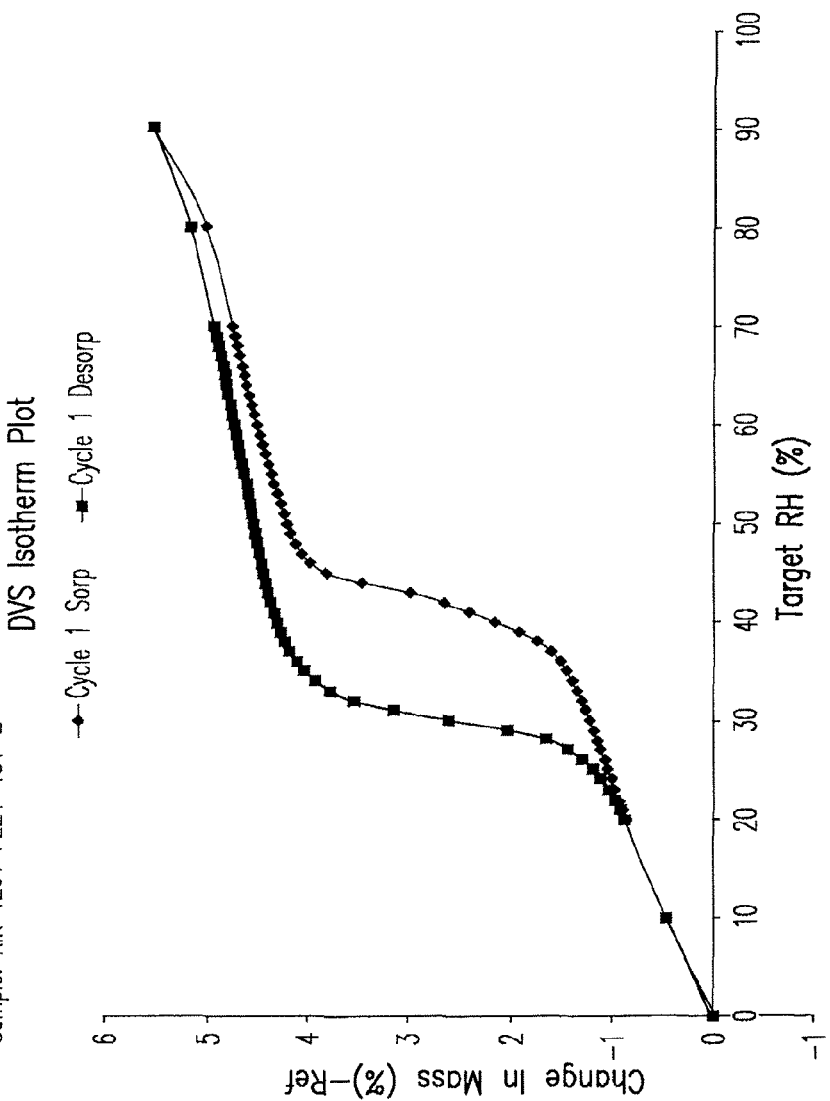

Assessment of the critical water activity using small equilibration steps (1% RH) with DVS measurements of sorption and desorption isotherms (FIG. 6) shows that this activity for transition between P-2 hydrate and anhydrous forms is typically between 30-40% RH. The characteristic gravimetric loss of water is between 1-4.5% w/w.

Figure 7:
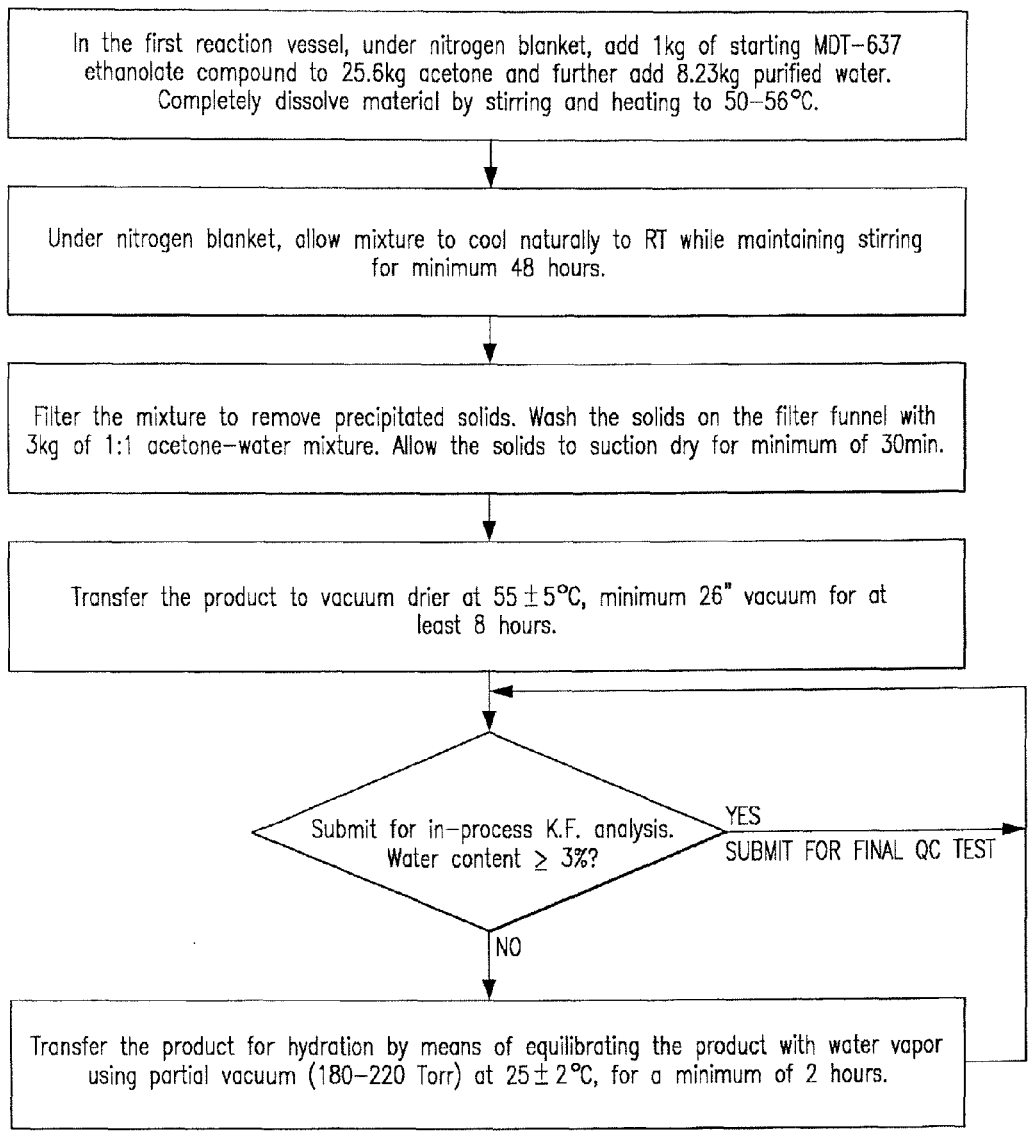

The manufacture of specific forms herein was controlled through the understanding of their thermodynamic relationship (phase diagram) and through the kinetics of crystallization process. The high purity material of pattern P-2 hydrate was recrystallized from P-3 ethanolate form dissolved in acetone/water mixture using water as an antisolvent with parallel cooling crystallization as disclosed in FIG. 7. The product was filtered, washed and dried under controlled conditions. The absence of ethanol was determined by $^1$H NMR analysis. The chemical purity of the material produced was determined using an HPLC method and preferable above 99.0%.

P-2 anhydrous form can be obtained from the P-2 hydrate by dehydrating this material below 30% RH and/or by heating it above 60° C.

Figure 8:
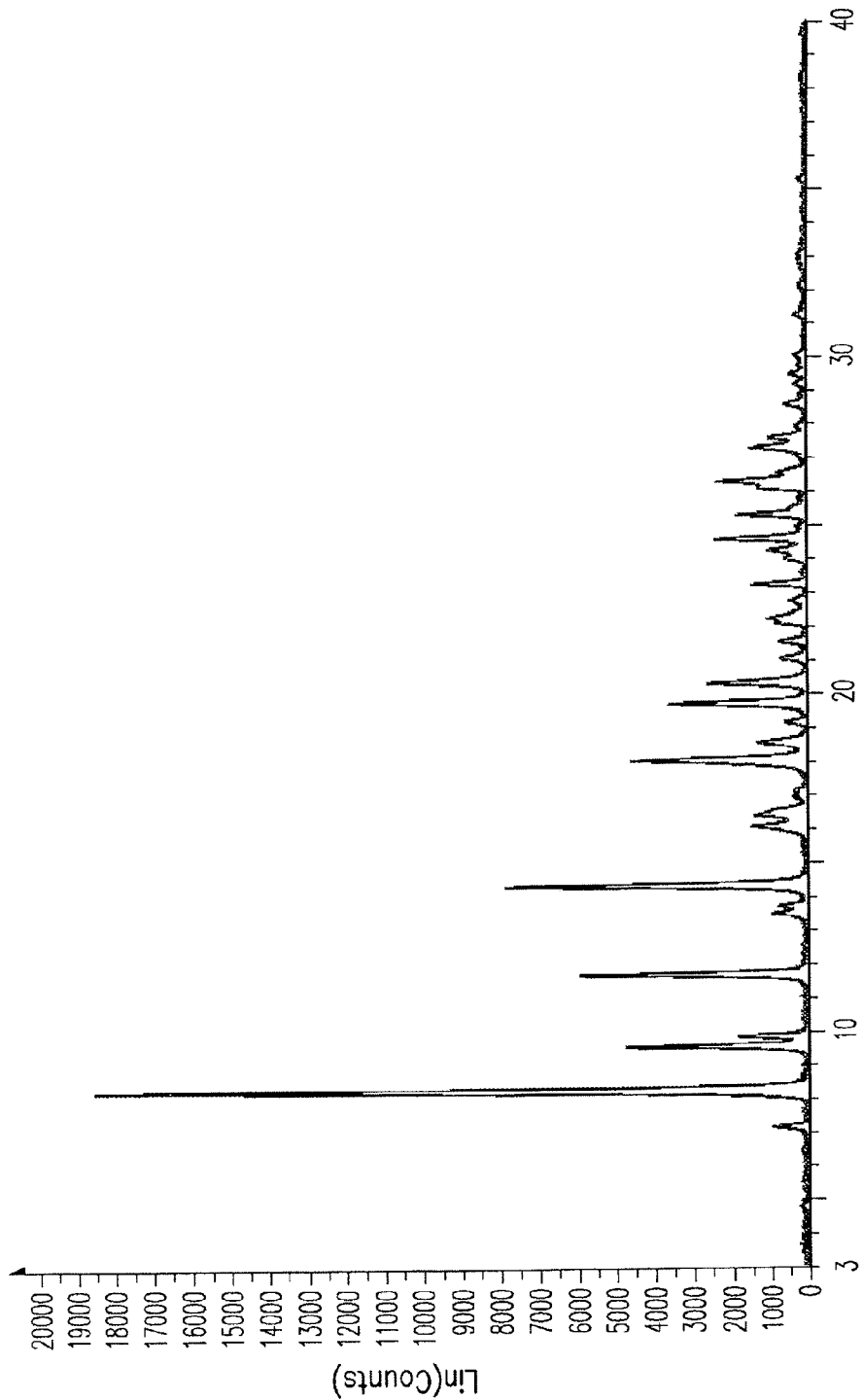
Figure 9:
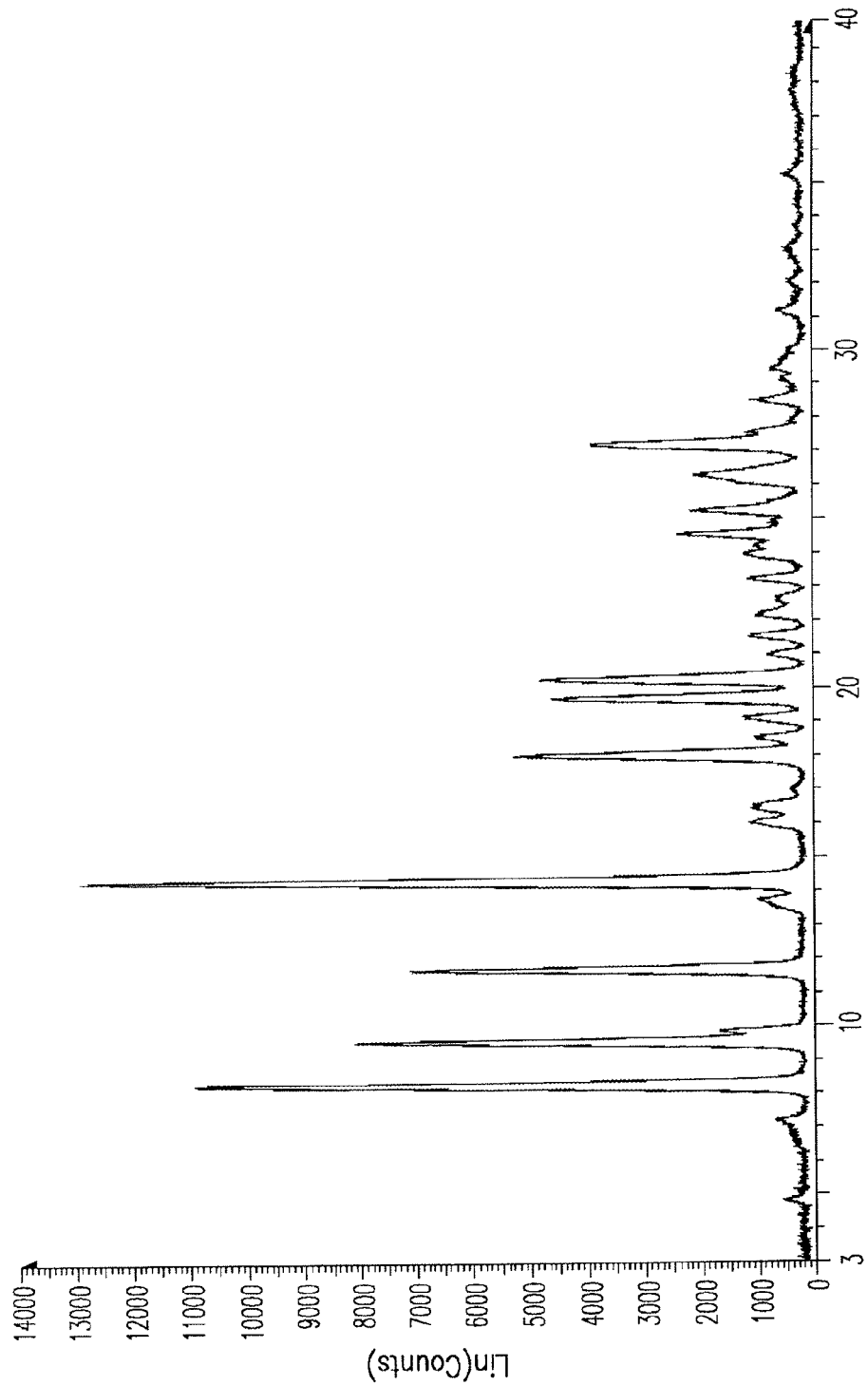
Figure 10:
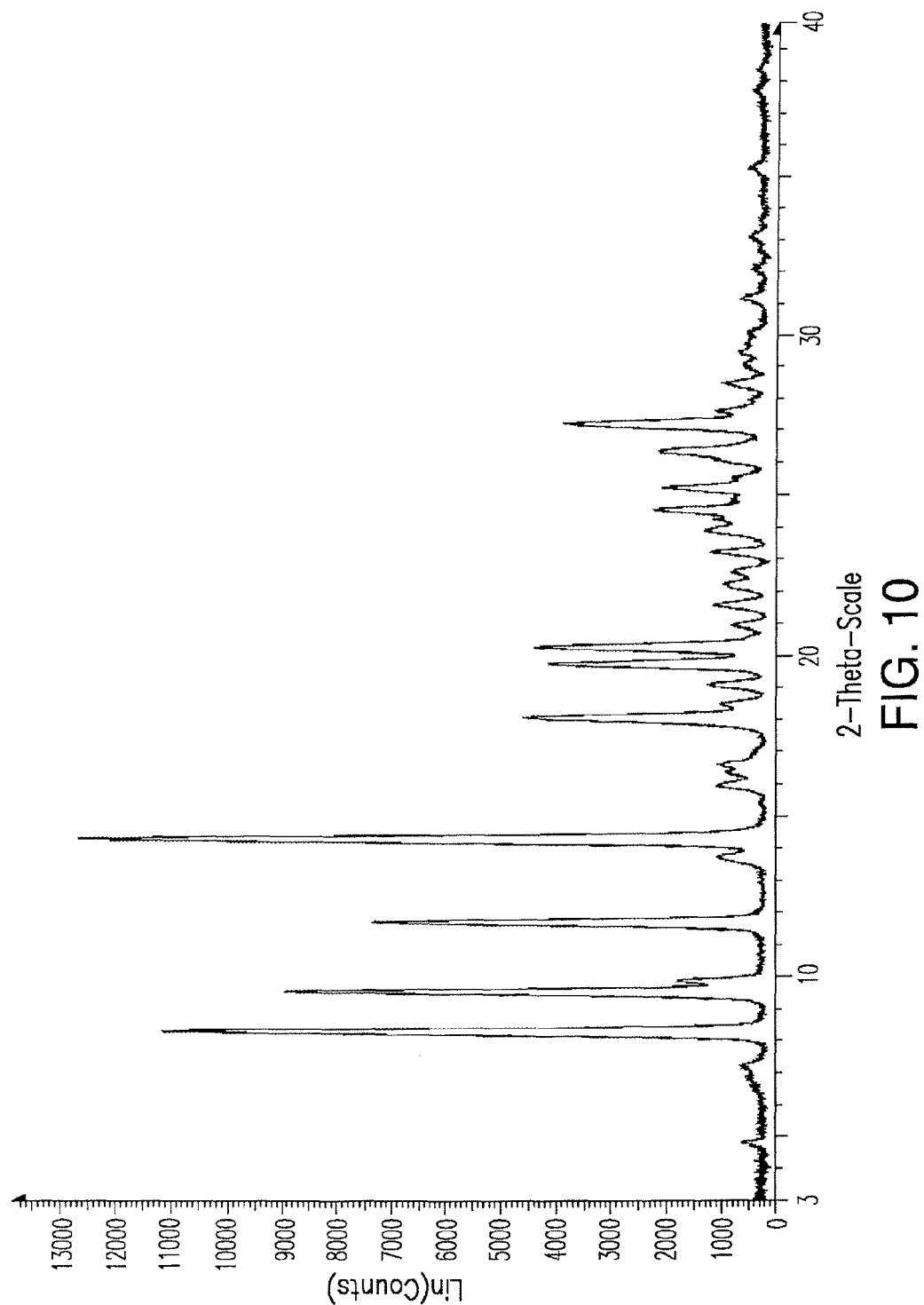
Figure 11:
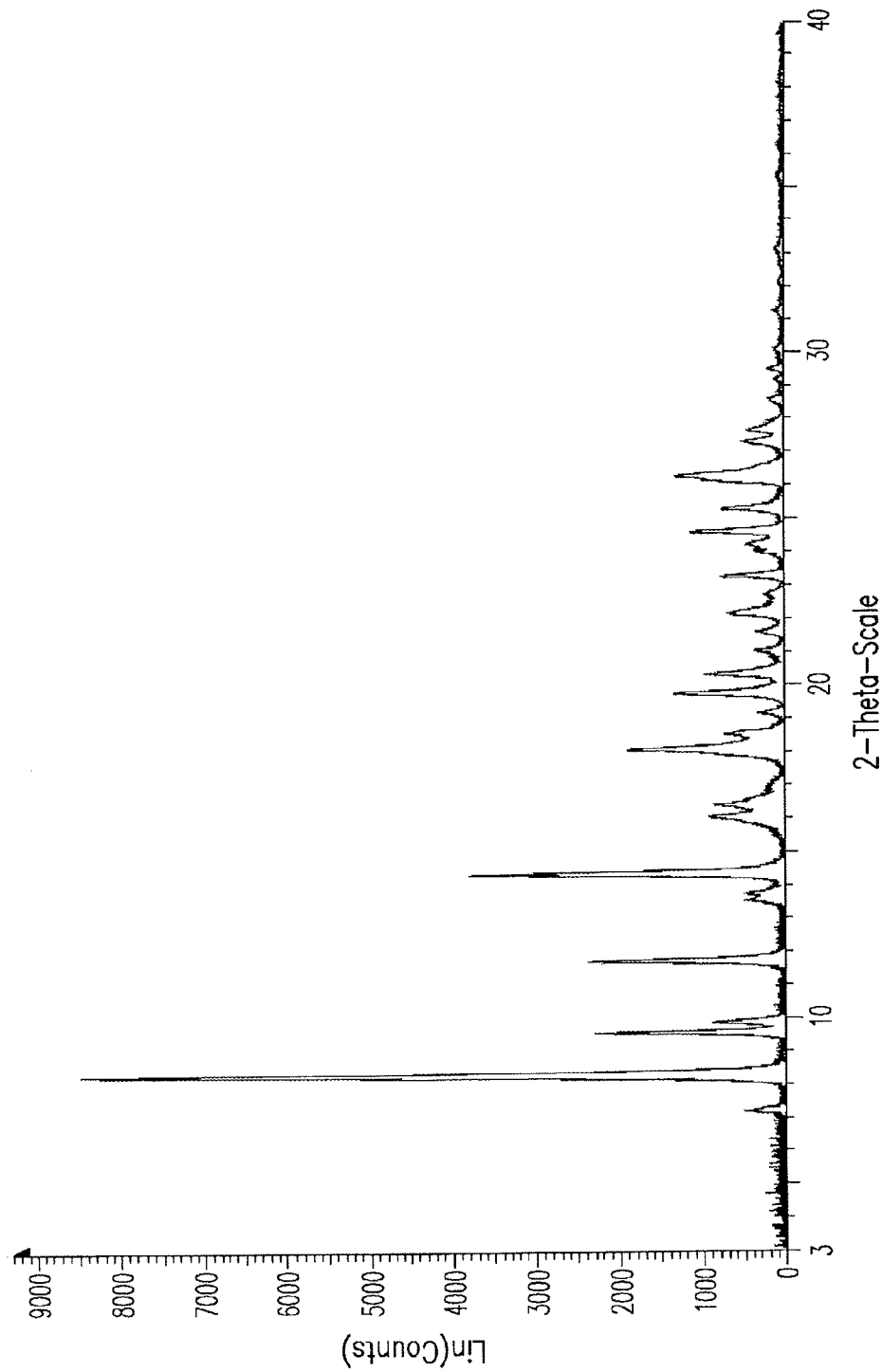

The characteristic diffraction peaks of the dihydrate crystal form of pattern P-3 are shown in FIG. 8 and listed in TABLE 3. The most characteristic peaks for P-3 dihydrate are observed at 2θ values: 7.03°; 8.16°; double peak at 9.47° and 9.75°; 11.60°; 14.24°; 17.95°, 19.64°; 20.26°; 24.52°; 26.24°; 27.25°. All crystal forms of pattern P-3 are isomorphic and therefore their PXRD patterns are similar and the corresponding peak values are very close to each other for P-3 dihydrate (FIG. 8, TABLE 3), monohydrate (FIG. 9; TABLE 4); anhydrous (FIG. 10; TABLE 5) as well as ethanolate (FIG. 11; TABLE 6) crystal forms. As discussed before, the peak position is affected by the accuracy of the PXRD instrument, sample preparation and by the peak fitting procedure. Therefore a deviation in measured peak positions is expected. However a specific PXRD pattern can easily be recognizable by one skilled in the art by considering peak positions together with peak intensities and correlating one PXRD pattern to a reference pattern.

TABLE 3

P-3 (Dihydrate Crystal Form) Characteristic Diffraction Peaks

| 2Θ, ° | d-value, Å | Relative Intensity % |
|---|---|---|
| 4.77 | 18.52 | 3.20 |
| 7.03 | 12.57 | 4.80 |
| 8.16 | 10.83 | 100.00 |
| 9.47 | 9.33 | 24.20 |
| 9.75 | 9.07 | 10.80 |
| 11.60 | 7.63 | 30.90 |
| 13.38 | 6.61 | 5.20 |
| 13.64 | 6.49 | 4.90 |
| 14.24 | 6.22 | 40.30 |
| 15.96 | 5.55 | 8.60 |
| 16.37 | 5.41 | 7.20 |
| 16.94 | 5.23 | 1.30 |
| 17.95 | 4.94 | 24.70 |
| 18.47 | 4.80 | 7.20 |
| 19.08 | 4.65 | 3.00 |
| 19.64 | 4.52 | 19.50 |
| 20.26 | 4.38 | 13.50 |
| 20.96 | 4.24 | 3.60 |
| 21.48 | 4.13 | 3.40 |
| 22.12 | 4.01 | 5.40 |
| 22.64 | 3.92 | 2.40 |
| 23.19 | 3.83 | 9.30 |
| 23.93 | 3.71 | 3.50 |
| 24.17 | 3.68 | 6.20 |
| 24.52 | 3.63 | 15.20 |
| 25.26 | 3.52 | 9.50 |
| 26.24 | 3.39 | 15.40 |
| 27.25 | 3.27 | 6.80 |
| 27.54 | 3.24 | 6.40 |
| 28.52 | 3.13 | 2.80 |
| 29.12 | 3.06 | 1.90 |
| 29.46 | 3.03 | 2.40 |
| 29.96 | 2.98 | 1.80 |
| 31.22 | 2.86 | 1.50 |

TABLE 4

P-3 (Monohydrate Crystal Form) Characteristic Diffraction Peak

| 2Θ, ° | d-value, Å | Relative Intensity % |
|---|---|---|
| 4.80 | 18.38 | 3.10 |
| 7.06 | 12.51 | 3.10 |
| 8.25 | 10.71 | 87.10 |
| 9.55 | 9.26 | 64.50 |
| 9.84 | 8.98 | 12.80 |
| 11.66 | 7.58 | 53.50 |
| 13.58 | 6.51 | 5.10 |
| 14.30 | 6.19 | 100.00 |
| 16.02 | 5.53 | 8.60 |
| 16.47 | 5.38 | 8.60 |
| 17.05 | 5.20 | 3.20 |
| 18.03 | 4.92 | 41.50 |
| 18.54 | 4.78 | 7.30 |
| 19.13 | 4.64 | 8.90 |
| 19.70 | 4.50 | 35.60 |
| 20.29 | 4.37 | 37.80 |
| 21.00 | 4.23 | 5.30 |
| 21.54 | 4.12 | 7.70 |
| 22.24 | 3.99 | 5.90 |
| 22.66 | 3.92 | 3.80 |
| 23.25 | 3.82 | 7.80 |
| 24.02 | 3.70 | 8.20 |
| 24.55 | 3.62 | 16.90 |
| 25.29 | 3.52 | 16.10 |
| 26.31 | 3.39 | 14.80 |
| 27.26 | 3.27 | 30.30 |
| 27.63 | 3.23 | 7.40 |
| 28.56 | 3.12 | 7.30 |
| 29.17 | 3.06 | 3.30 |
| 29.53 | 3.02 | 4.40 |
| 31.25 | 2.86 | 3.50 |

TABLE 5

P-3 (Anhydrous Crystal Form) Characteristic Diffraction Peaks

| 2Θ, ° | d-value, Å | Relative Intensity % |
|---|---|---|
| 4.77 | 18.52 | 3.20 |
| 7.08 | 12.48 | 2.80 |
| 8.27 | 10.68 | 88.70 |
| 9.54 | 9.27 | 71.40 |
| 9.86 | 8.96 | 13.40 |
| 11.68 | 7.57 | 58.30 |
| 13.73 | 6.44 | 8.00 |
| 14.29 | 6.19 | 100.00 |
| 15.96 | 5.55 | 7.30 |
| 16.38 | 5.41 | 5.80 |
| 16.62 | 5.33 | 7.30 |
| 18.07 | 4.90 | 34.70 |
| 18.51 | 4.79 | 6.90 |
| 19.09 | 4.65 | 8.00 |
| 19.79 | 4.48 | 32.30 |
| 20.30 | 4.37 | 34.20 |
| 20.97 | 4.23 | 5.20 |
| 21.58 | 4.11 | 7.80 |
| 22.23 | 4.00 | 6.30 |
| 22.63 | 3.93 | 5.20 |
| 23.25 | 3.82 | 8.00 |
| 23.98 | 3.71 | 8.50 |
| 24.54 | 3.62 | 15.90 |
| 25.27 | 3.52 | 15.30 |
| 26.36 | 3.38 | 15.60 |
| 27.25 | 3.27 | 28.30 |
| 27.67 | 3.22 | 7.50 |
| 28.51 | 3.13 | 5.60 |
| 29.13 | 3.06 | 3.50 |
| 29.57 | 3.02 | 3.70 |
| 30.10 | 2.97 | 3.30 |
| 31.20 | 2.86 | 3.50 |

TABLE 6

P-3 (Ethanolate Form) Characteristic Diffraction Peaks

| 2Θ, ° | d-value, Å | Relative Intensity, % |
|---|---|---|
| 7.16 | 12.34 | 5.80 |
| 8.25 | 10.71 | 100.00 |
| 9.54 | 9.26 | 27.40 |
| 9.85 | 8.98 | 10.80 |
| 11.69 | 7.57 | 27.80 |
| 13.47 | 6.57 | 6.20 |
| 13.74 | 6.44 | 6.20 |
| 14.32 | 6.18 | 44.80 |
| 15.99 | 5.54 | 11.30 |
| 16.45 | 5.39 | 10.50 |
| 18.06 | 4.91 | 22.20 |
| 18.51 | 4.79 | 9.40 |
| 19.16 | 4.63 | 4.30 |
| 19.73 | 4.50 | 15.60 |
| 20.33 | 4.36 | 11.10 |
| 20.97 | 4.23 | 3.10 |
| 21.56 | 4.12 | 4.60 |
| 22.17 | 4.01 | 8.00 |
| 22.67 | 3.92 | 3.50 |
| 23.27 | 3.82 | 8.20 |
| 24.19 | 3.68 | 6.20 |
| 24.54 | 3.62 | 10.70 |
| 25.29 | 3.52 | 8.60 |
| 26.27 | 3.39 | 15.50 |
| 27.32 | 3.26 | 6.70 |
| 27.67 | 3.22 | 5.60 |
| 28.57 | 3.12 | 2.00 |
| 29.19 | 3.06 | 1.90 |
| 29.46 | 3.03 | 2.10 |
| 30.06 | 2.97 | 1.20 |
| 31.26 | 2.86 | 1.50 |

Figure 12:
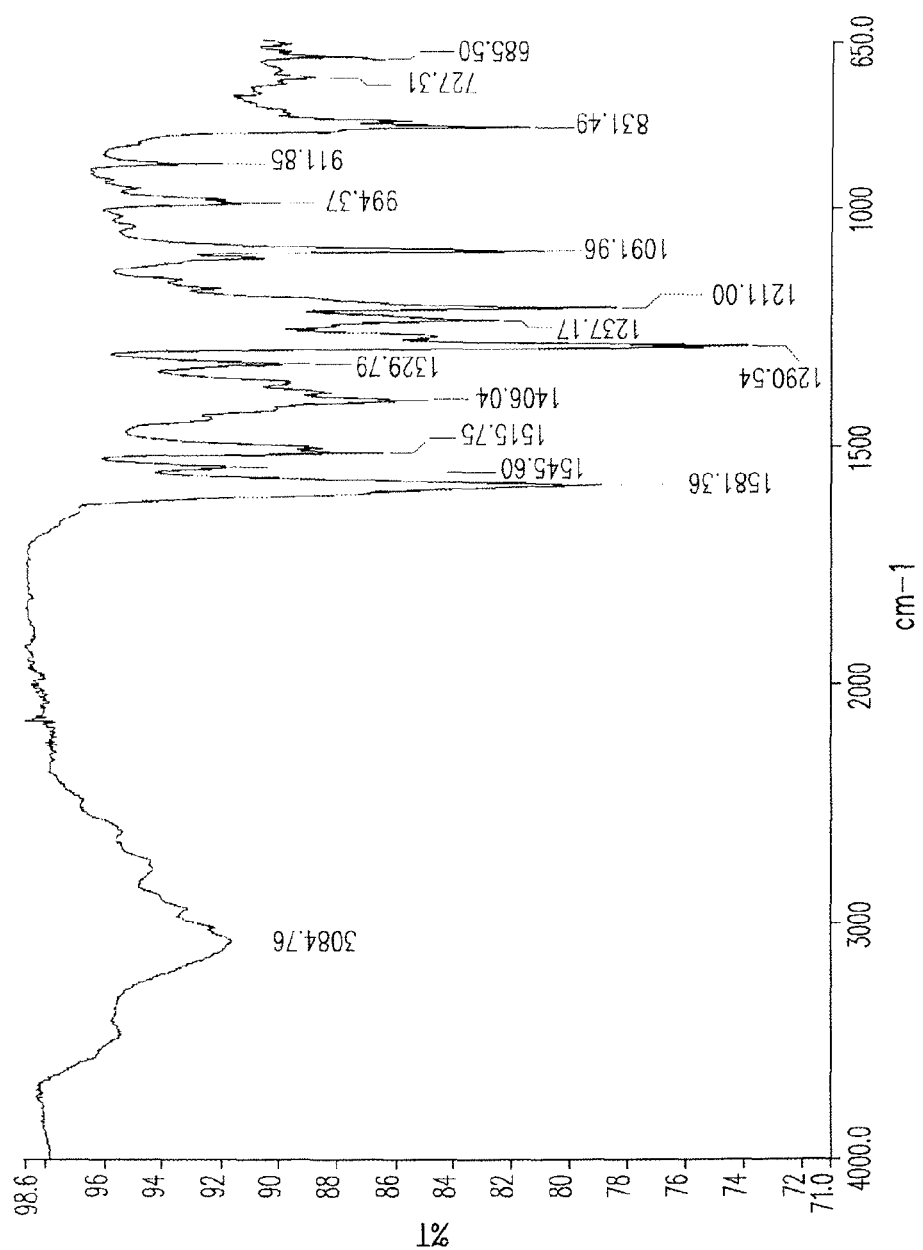

FIG. 12 represents a characteristic FTIR pattern of the P-3 hydrate. The most characteristic absorption bands in the region are between 800-1200 $cm^{-1}$, corresponding to P-3 crystal forms are: 831.5 $cm^{-1}$; 994.9 $cm^{-1}$, 1092.0 $cm^{-1}$, 1211.0 $cm^{-1}$, 1237.7 $cm^{-1}$ and 1290.5 $cm^{-1}$.

Figure 13:
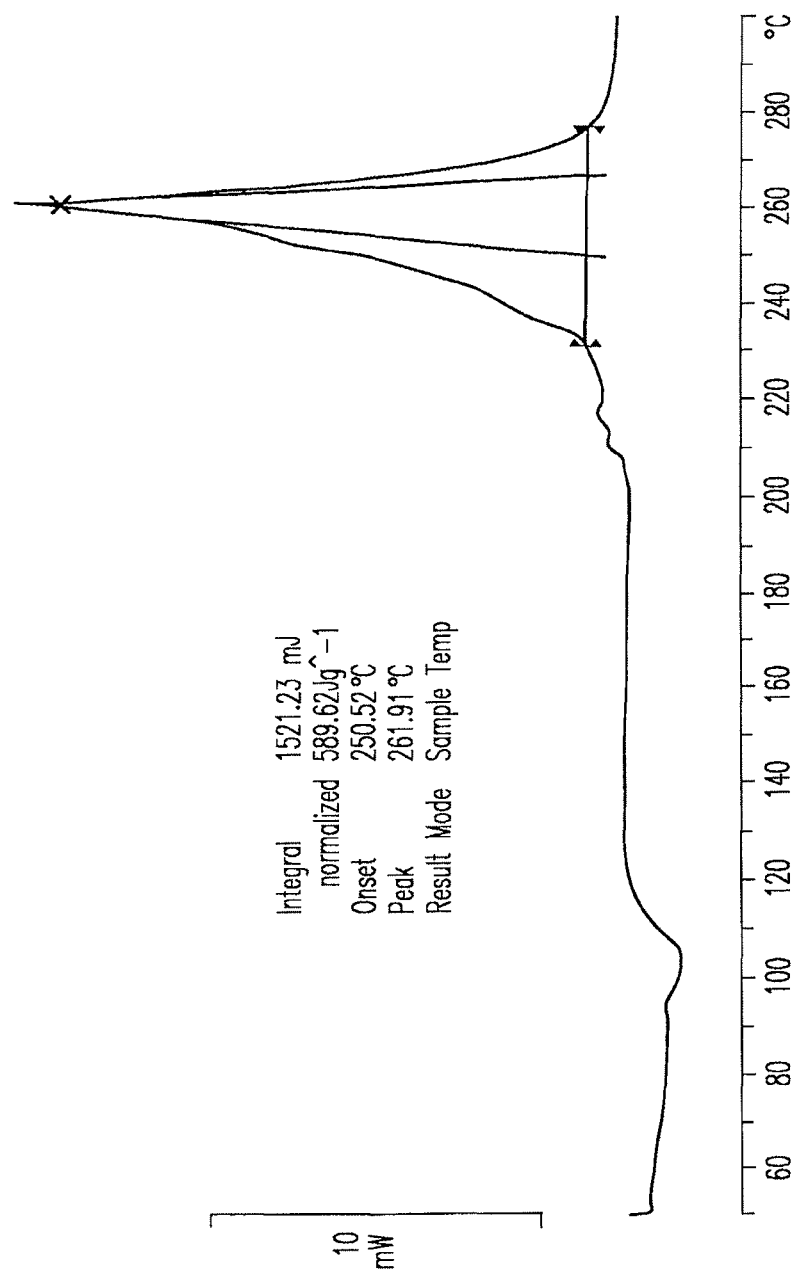
Figure 14:
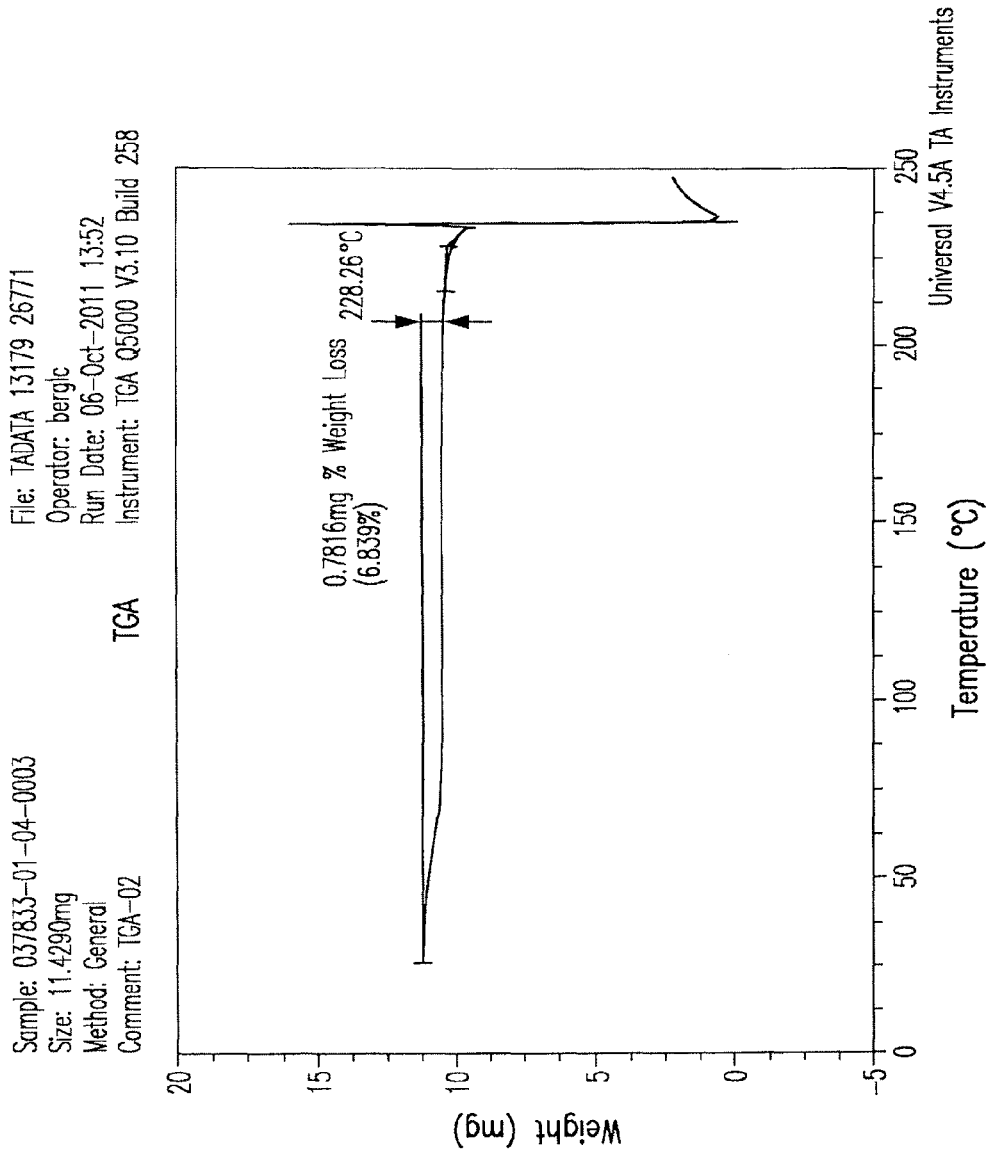

DSC trace for P-3 dihydrate (FIG. 13) exhibits a wide endothermic event between 220° C. to 280° C., the characteristic delta-shaped peak of which suggests several thermal events, such as recrystallization/transition between different forms, in this interval. TGA data shows weight loss of 5-7% between 30° C. to 100° C. for this material (FIG. 14). Therefore P-3 dihydrate loses water at a higher temperature than P-2 hydrate but undergoes some additional changes after this event and the melting peak may correspond to a different form.

Figure 15:
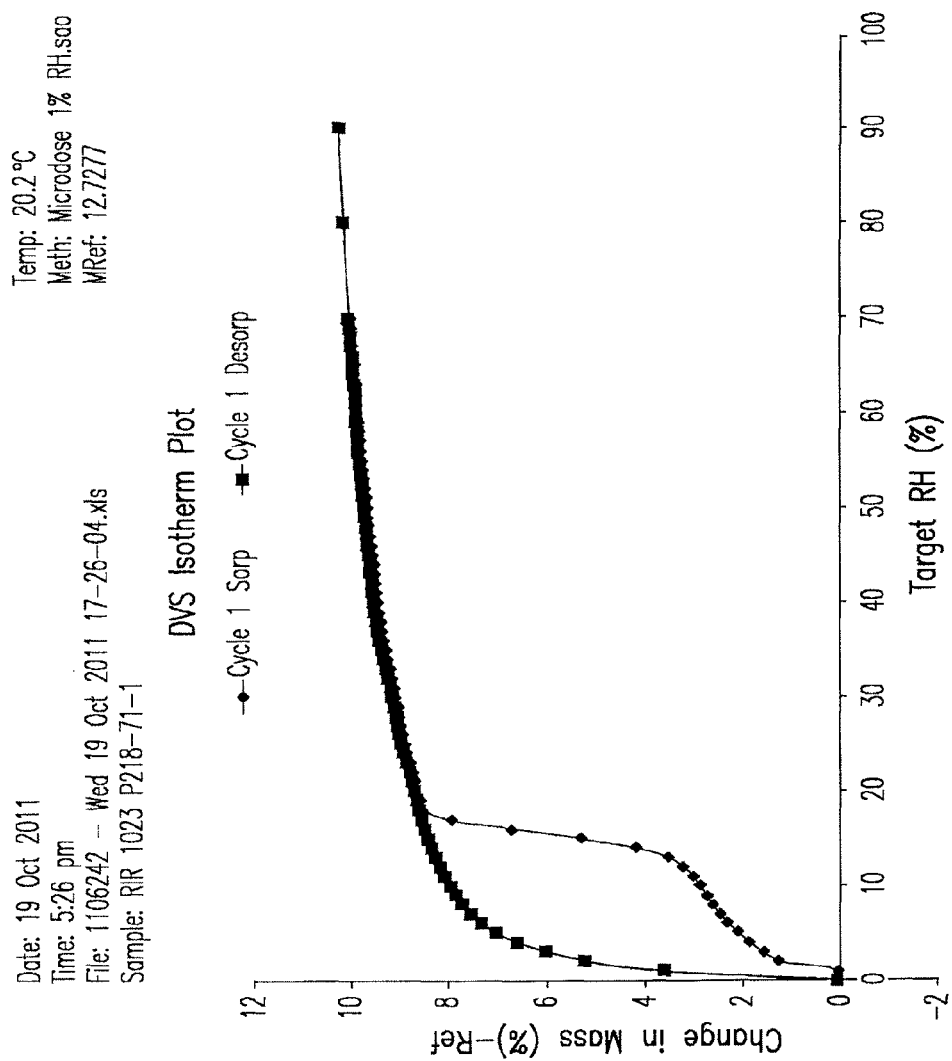

Assessment of the critical water activity using small equilibration steps (1% RH) with DVS measurements of sorption and desorption isotherms for P-3 forms (FIG. 15) shows two transition points (mono- and dihydrate) at approximately 3 and 13% RH. The characteristic gravimetric loss of water for P-3 dihydrate is between 5.5-8.5% w/w. The profound difference of the DVS curves between the P-2 and P-3 forms can be utilized as a secondary technique for quantitative phase analysis of these forms.

Figure 16:
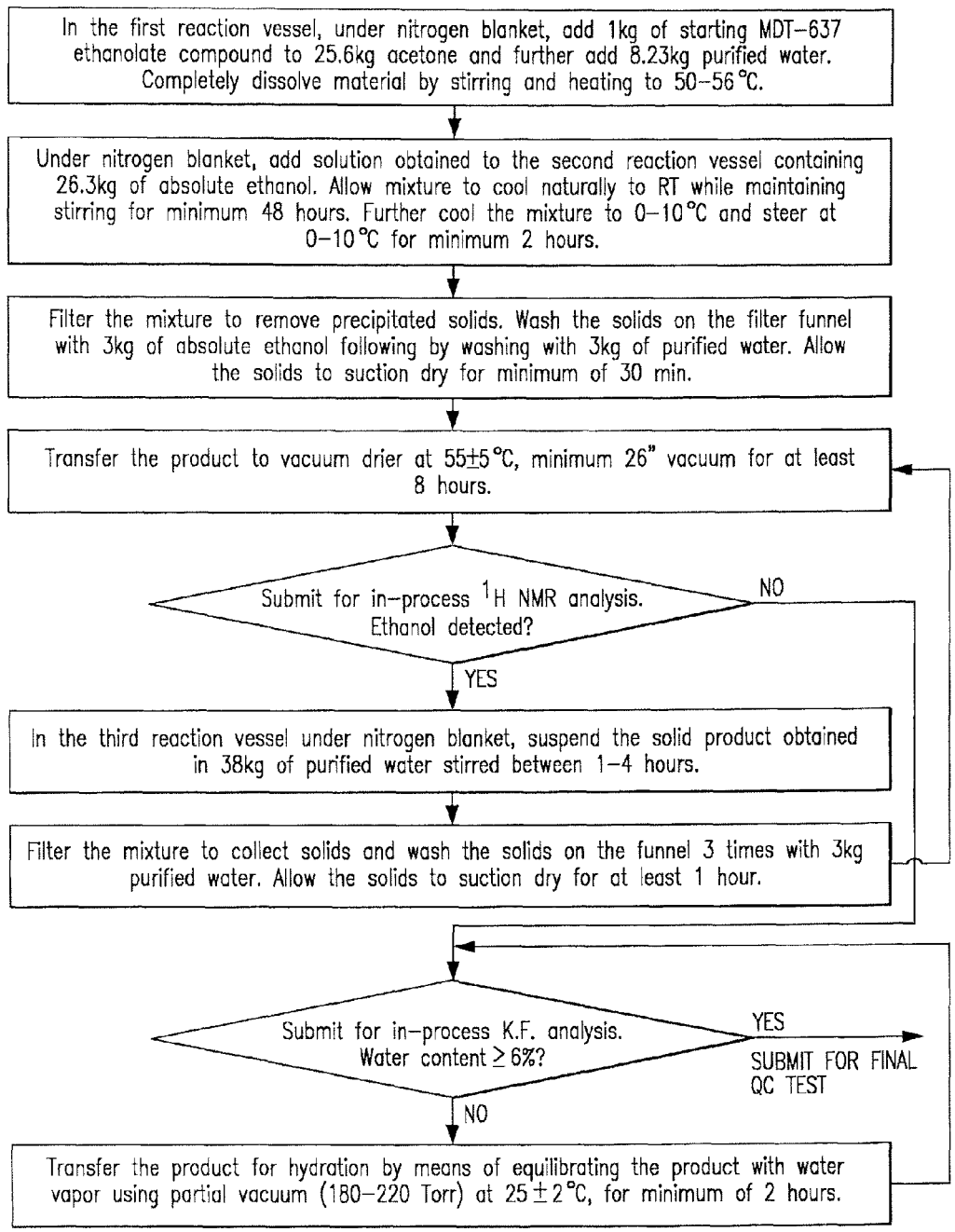

P-3 ethanolate was obtained by crystallization from solution containing sufficient amount of ethanol above a certain critical concentration. This critical concentration in acetone/water/ethanol system, used both for the API purification and generation of P-3 ethanolate form, was found to be approximately 33% v/v. A reproducible crystallization process was achieved at ethanol concentrations above this limit. FIG. 16 illustrate the process for production of high purity P-3 dihydrate which is obtained by recrystallization of P-3 ethanolate dissolved in acetone/water mixture using ethanol as an antisolvent with parallel cooling crystallization, following by filtration, washing, hydration and drying steps under controlled conditions. The absence of ethanol is determined by $^1H$ NMR analysis. The chemical purity of the material produced is determined using an HPLC method and preferably above 99.0%.

P-3 monohydrate and P-3 anhydrous forms can be obtained from the P-3 dihydrate by drying this material below approximately 13% RH for monohydrate and below approximately 3% RH for anhydrous form and/or by prolonged heating it at elevated temperatures preferably above 60° C.

Figure 17:
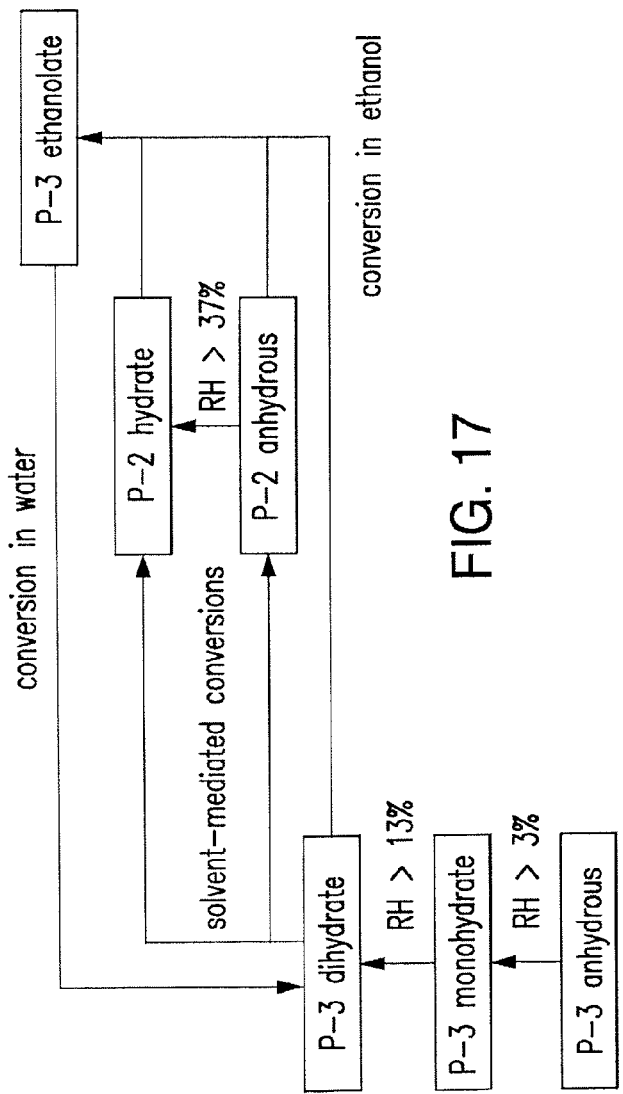

It was discovered that P-2 dihydrate is the most stable crystal form under ambient conditions (i.e. temperatures preferably between 15-37° C., relative humidity preferably between 40-100%). It was also discovered that P-3 ethanolate is the most stable crystal form with sufficient activity of ethanol (sufficiently high concentration of ethanol in solution) preferably above 0.3. FIG. 17 shows a diagram of thermodynamic relationship between different P-2 and P-3 forms.

Figure 18A:
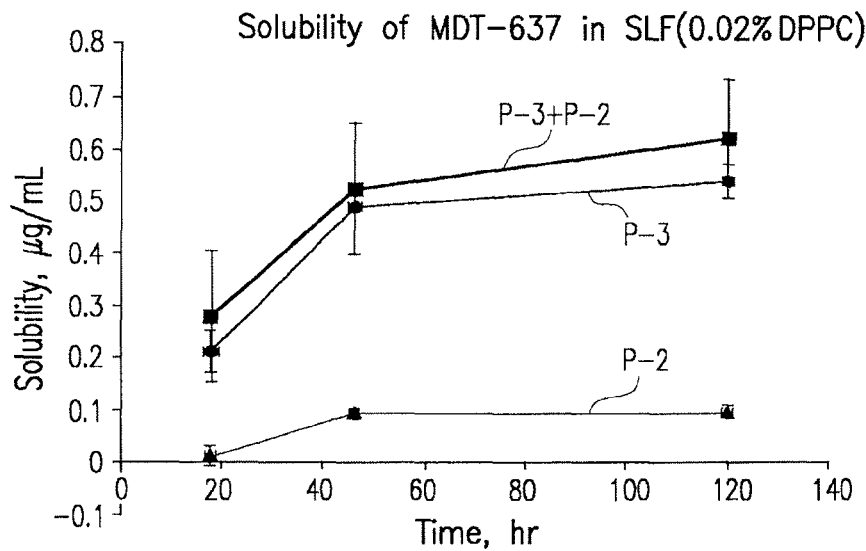
Figure 18B:
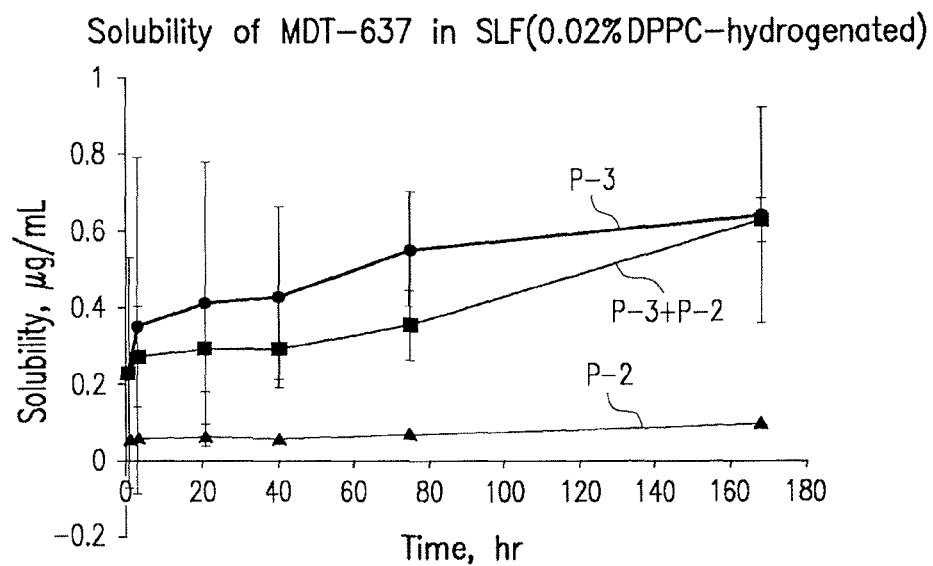

Time-dependent solubility study was carried out in simulated lung fluid (SLF) containing the surfactant dipalmitoylphosphatidylcholine (DPPC). The DPPC is a major surfactant present in the human lung. Since MDT-637 is formulated for delivery through nasal passage to the lung, it is very important to have the API solubility assessed in SLF modified with 0.02% DPPC as such information is useful in understanding the drug functionality in the lung. FIG. 18 shows results of dissolution studies carried out for 5 days with two different DPPC surfactants at concentration 0.02% w/v, and with P-2 hydrate, P-3 dihydrate and mixed P-3/P-2 material at 37° C. The data indicates that the solubility of P-3 dihydrate is approximately 550 ng/mL (1077 nM) versus 100 ng/mL (196 nM) for P-2 hydrate. Solubility in pure water, also assessed during these studies for both P-2 and P-3 forms, is significantly lower: it is below the HPLC limit of detection, approximately equivalent to 6 nM. These results indicate, firstly, that P-2 form is approximately a factor of 5 to 6 lower than solubility of P-3 dihydrate.

In addition, P-3 dihydrate material was stable against solid-state changes and chemical degradation in open-dish stability studies at 40° C./75% RH for 4 weeks as shown in the Examples.

P-3 dihydrate material was also stable against solid-state conversion in formulation with lactose while stored in sealed glass bottles for 39 weeks at 40° C./75% RH as shown in the Examples.

Furthermore, micronization did not affect the crystallinity, phase purity or induce any chemical degradation for P-3 dihydrate as shown in the Examples.

Following the experiments discussed above, it was therefore discovered that P-3 dihydrate, despite being a less thermodynamically stable form than P-2 hydrate, is kinetically stable to solid-state conversions, dehydration and chemical degradation, and possesses the advantage of significantly higher solubility than P-2 hydrate form. P-3 dihydrate is therefore a sufficiently robust and suitable crystal form for pharmaceutical development. Comparison of some major physicochemical properties of P-3 dehydrate versus P-2 hydrate is presented in TABLE 7.

TABLE 7

| | | Characteristics | |
|---|---|---|---|
| Property | Method | P-2 hydrate | P-3 dihydrate |
| Appearance | N/A | white solid | white solid |
| Crystal habit | Microscopy | acicular | acicular |
| Melting point | DSC | 263° C. | range: 220-280° C. |
| Characteristic relative humidity of dehydration (20° C.) | DVS | 30-40% | 3-17% |
| Water content | Stoichiometric | 3.3 wt % (monohydrate) | 6.6 wt % |
| Crystal (skeletal) density | Nitrogen Pycnometry | $g/cm^3$ | 1.61 $g/cm^3$ |
| Characteristic medium volume particle size (micronized) | Sympatec HELOS & RODOS | 1.1 μm | 1.5 μm |
| Specific surface area | BET | 22.6 $m^2/g$ | 11.0 $m^2/g$ |
| Poured bulk powder density | Volumetric | 0.16 $g/cm^3$ | 0.22 $g/cm^3$ |
| Tapped bulk powder density | Volumetric | 0.19 $g/cm^3$ | 0.30 $g/cm^3$ |
| Hausner ratio | Volumetric | 1.20 | 1.38 |
| Carr index | Volumetric | 16.7% | 27.5% |

As recognized by those skilled in the art, the polymorphic form chosen is typically the most thermodynamically stable form because higher solubility or superior powder characteristics of some metastable forms usually do not justify the regulatory risks associated with uncontrollable conversion of such forms in the final drug product, either during their processing and/or storage. However, in contrast to what would be expected, the inventors herein selected the less thermodynamically stable form, P-3 dihydrate for a preferred embodiment, considering it to represent a more viable option for product development as discussed above and in the Examples. Although development of a less stable solid form is not advisable, the risk of multifold reduction in solubility, and potentially drug concentration against the clinical strains of RSV is significant.

In addition to the crystal forms of the P-2 and P-3 patterns, other novel crystal forms were discovered, these include but are not limited to, P-4, P-6, P-7 and P-8.

The characteristic diffraction peaks of crystal form of pattern P-4 are shown in FIG. 19 and TABLE 8. The most characteristic peaks for P-4 form are observed at 2θ values: 4.31°, 7.99°, 9.37°, 11.02°, 13.04°, 13.43°, 14.18°, 16.13°, 16.70°, 17.08°, 17.42°, 17.92°. This form was obtained from saturated DMF solution using cooling, evaporation or anti-solvent crystallization procedures. Though not wishing to be bound by any particular theory, it is believed that P-4 crystal form is likely a DMF solvate.

TABLE 8

P-4 (Crystal Form) Characteristic Diffraction Peaks Pattern

| 2Θ, ° | d-value, Å | Relative Intensity % |
|---|---|---|
| 4.31 | 20.49 | 22.00 |
| 7.03 | 12.57 | 5.40 |
| 7.99 | 11.06 | 100.00 |
| 8.92 | 9.90 | 3.00 |
| 9.37 | 9.43 | 16.60 |
| 11.02 | 8.02 | 8.90 |
| 13.04 | 6.78 | 9.40 |
| 13.43 | 6.59 | 11.60 |
| 13.69 | 6.46 | 6.70 |
| 14.18 | 6.24 | 12.60 |
| 14.76 | 6.00 | 3.80 |
| 16.13 | 5.49 | 15.10 |
| 16.70 | 5.30 | 21.00 |
| 17.08 | 5.19 | 17.50 |
| 17.42 | 5.09 | 51.60 |
| 17.92 | 4.95 | 8.90 |
| 18.84 | 4.71 | 7.00 |
| 19.18 | 4.62 | 7.00 |
| 20.50 | 4.33 | 11.30 |
| 22.39 | 3.97 | 1.50 |
| 22.99 | 3.87 | 2.50 |
| 24.09 | 3.69 | 2.70 |
| 25.07 | 3.55 | 4.70 |
| 25.61 | 3.48 | 5.20 |
| 27.40 | 3.25 | 5.00 |
| 28.30 | 3.15 | 10.40 |
| 29.49 | 3.03 | 1.40 |

The characteristic diffraction peaks of crystal form of pattern P-6 are shown in FIG. 20 and TABLE 9. The most characteristic peaks for P-6 form are observed at 2θ values: double peak at 3.43° and 3.89°, 6.89°, double peak at 7.87° and 8.25°, 10.88°, 13.06° and 13.81°, 16.12° 17.38° and 18.51°. This form was obtained from saturated DMF solution using antisolvent crystallization with MTBE.

TABLE 9

P-6 (Crystal Form) Characteristic Diffraction Peaks Pattern

| 2Θ, ° | d-value, Å | Relative Intensity % |
|---|---|---|
| 3.43 | 25.71 | 100.00 |
| 3.89 | 22.69 | 53.20 |
| 6.89 | 12.83 | 4.70 |
| 7.87 | 11.23 | 18.10 |
| 8.25 | 10.72 | 8.20 |
| 9.31 | 9.49 | 1.90 |
| 9.92 | 8.91 | 1.60 |
| 10.88 | 8.13 | 3.20 |

TABLE 9-continued

P-6 (Crystal Form) Characteristic Diffraction Peaks Pattern

| 2Θ, ° | d-value, Å | Relative Intensity % |
|---|---|---|
| 13.06 | 6.78 | 2.80 |
| 13.81 | 6.41 | 4.00 |
| 16.12 | 5.49 | 11.10 |
| 17.38 | 5.10 | 37.50 |
| 18.51 | 4.79 | 9.20 |
| 20.25 | 4.38 | 2.30 |
| 22.02 | 4.03 | 1.50 |
| 22.83 | 3.89 | 2.20 |
| 25.23 | 3.53 | 5.90 |
| 27.52 | 3.24 | 4.80 |
| 28.18 | 3.16 | 3.60 |

The characteristic diffraction peaks of crystal form of pattern P-7 are shown in FIG. 21 and TABLE 10. The most characteristic peaks for P-7 form are observed at 2θ values: 5.18°, 6.59°, 7.70°, double peak 10.02 and 10.62°, double peak at 12.18° and 12.50°, 15.16°, double peak at 15.88° and 16.4°, double peak at 17.20 and 17.42°, double peak at 18.07° and 18.25°. This form was obtained from saturated NMP solution by antisolvent precipitation in two-phase ternary system NMP-cyclohexane-water.

TABLE 10

P-7 (Crystal Form) Characteristic Diffraction Peaks Pattern

| 2Θ, ° | d-value, Å | Relative Intensity % |
|---|---|---|
| 5.18 | 17.03 | 37.60 |
| 6.59 | 13.40 | 100.00 |
| 7.70 | 11.47 | 7.50 |
| 10.02 | 8.82 | 46.00 |
| 10.62 | 8.33 | 30.20 |
| 12.18 | 7.26 | 28.00 |
| 12.50 | 7.07 | 17.40 |
| 13.40 | 6.60 | 6.50 |
| 15.16 | 5.84 | 59.50 |
| 15.88 | 5.58 | 73.40 |
| 16.40 | 5.40 | 13.00 |
| 17.20 | 5.16 | 32.00 |
| 17.42 | 5.09 | 90.70 |
| 18.07 | 4.91 | 27.30 |
| 18.25 | 4.86 | 20.00 |
| 19.57 | 4.53 | 4.80 |
| 20.26 | 4.38 | 13.70 |
| 21.35 | 4.16 | 15.40 |
| 21.94 | 4.05 | 30.70 |
| 22.76 | 3.90 | 10.00 |
| 23.34 | 3.81 | 24.80 |
| 24.02 | 3.70 | 8.90 |
| 24.46 | 3.64 | 9.90 |
| 25.25 | 3.52 | 18.00 |
| 26.11 | 3.41 | 9.30 |
| 26.70 | 3.34 | 6.90 |
| 28.11 | 3.17 | 13.30 |
| 28.87 | 3.09 | 4.40 |
| 29.35 | 3.04 | 1.90 |
| 29.86 | 2.99 | 1.80 |
| 30.69 | 2.91 | 3.20 |
| 31.90 | 2.80 | 2.20 |
| 33.07 | 2.71 | 1.00 |
| 35.46 | 2.53 | 2.20 |

The characteristic diffraction peaks of crystal form of pattern P-8 are shown in FIG. 22 and TABLE 11. The most characteristic peaks for P-8 form are observed at 2θ values: 4.15°, 7.85°, 9.33°, 14.29°, triple peak at 15.84, 16.68 and 17.14°, 18.53°, 20.27°, 23.90°, 24.80° and 27.39°. This form was obtained from two different crystallization systems: first, antisolvent precipitation from saturated DMSO solution with addition of water and, second, by antisolvent precipitation from saturated DMF solution using acetone/water mixture as the antisolvent.

TABLE 11

P-8 (Crystal Form) Characteristic Diffraction Peaks Pattern

| 2Θ, ° | d-value, Å | Relative Intensity % |
|---|---|---|
| 4.15 | 21.30 | 18.40 |
| 6.89 | 12.81 | 3.30 |
| 7.85 | 11.25 | 65.30 |
| 9.33 | 9.47 | 30.90 |
| 11.67 | 7.58 | 15.20 |
| 12.86 | 6.88 | 4.30 |
| 14.29 | 6.20 | 100.00 |
| 15.84 | 5.59 | 22.80 |
| 16.68 | 5.31 | 50.00 |
| 17.14 | 5.17 | 69.10 |
| 18.53 | 4.78 | 12.10 |
| 20.27 | 4.38 | 21.50 |
| 21.06 | 4.21 | 8.90 |
| 22.00 | 4.04 | 6.50 |
| 22.72 | 3.91 | 8.90 |
| 23.90 | 3.72 | 29.80 |
| 24.80 | 3.59 | 16.10 |
| 27.39 | 3.25 | 21.50 |
| 28.32 | 3.15 | 9.80 |
| 30.03 | 2.97 | 3.20 |
| 31.83 | 2.81 | 3.50 |
| 35.22 | 2.55 | 2.70 |

The PXRD pattern of the amorphous form does not exhibit characteristic diffraction peaks but show "halos" with typically one or more maxima. The position of these maxima may vary depending on the preparation technique used for the amorphous material. The amorphous form can be obtained by several techniques including but not limited to: (a) rapid cooling of saturated API solution; (b) fast evaporation of API solutions; (c) fast antisolvent precipitation; (d) spray-drying and (b) freeze-drying. Examples are provided below.

"Solid composition" is yet another embodiment of the API. Similar to the amorphous form, solid composition may not produce a characteristic PXRD pattern identifiable with specific crystalline API diffraction peaks. One important aspect of this invention is the preparation methodology for the API: in certain embodiments, an excipient matrix, in the form of solid composite microparticles is used wherein the drug is blended into uniform solid phase with selected excipients. The excipients are selected in order to optimize various parameters, including but not limited to, drug dissolution rate, enabling mucoadhesive properties after the delivery of microparticles into biospaces, combining antiviral properties of excipients synergistically (to provide a more significant and/or prolonged therapeutic antiviral effect greater than that achieved by the API alone).

The processes for production of solid compositions include but not limited to several techniques: (a) rapid co-precipitation cooling during mixing of saturated API solution with saturated excipient solution; (b) fast evaporation of suitable API-excipient solutions; (c) spray-drying of suitable API-excipient solutions, (d) freeze-drying of suitable API-excipient solutions. Examples are provided below.

Solid compositions or formulations of the API with selected excipients which form composite solid microparticles, or films, or composite matrixes, where the drug and excipient are physically or chemically attached to each other within composite phase, whereas the excipients can be small molecules or macromolecular substances, including but not limited to different forms and chemical modifications of lactose, trehalose, sugars, mannitol, amino-acids, polymers including but not limited to different chemical modifications of hydroxypropylmethyl cellulose (HPMC) and microcrystalline cellulose with sodium carboxymethylcellulose (e.g. Avicel CL-611, RC-581, RC-591 available from FMC Inc. Philadelphia, Pa.), naturally occurring polysaccharides extracted from red seaweed (carrageenans) supplied by FMC Inc. as GELCARIN™, VISCARIN™, and SEASPEN PF™ carrageenans and different dispersing and wetting agents such as polysorbate 80, antioxidants (e.g. ascorbic acid, sodium ascorbate, sodium bisulfate, disodium ethylenediamine tetraacetate (EDTA) and osmolarity modifiers (e.g. dextrose).

In comparison to currently available therapeutics, the MDT-637 compounds described herein display significantly enhanced efficacy. The key efficacy features uniquely associated with the compounds include: reduction in hospitalization stay and progression to intensive care/ventilator, reduction in symptom duration and reduction in respiratory distress index. In addition, the compounds and compositions of the present invention are also effective against drug resistant strains of RSV, i.e. strains resistant to SYNAGIS® (palivizumab).

As described in the examples, and in particular Example 27, experiments and phase 1 clinical programs evaluating the safety of the MDT-637 compounds have been successfully completed. MDT-637 polymorphs such as MDT-637 P3 were determined to be safe and well tolerated in three doses up to 132 mcg TID for 10 days. In a first randomized double-blind placebo controlled study (Study 1), where MDT-637 was administered to healthy volunteers in single ascending doses, no clinically significant changes in pulmonary function, ECG, laboratory values vitals or physical examination were observed.

In a second study (Study 2) also designed to assess safety and tolerability MDT-637 was administered to healthy volunteers for ten days. Ascending doses were tested from 66 mcg twice daily to 132 mcg three times daily for ten days in approximately forty volunteers. The study findings demonstrated that MDT-637 was safe and well tolerated at doses up to 132 mcg three times daily for ten days; in addition no significant changes were observed in pulmonary function or reports of pulmonary adverse events.

In a third study (Study 3) further designed to assess safety and tolerability ascending doses of MDT-637 were administered to subjects with intermittent or mild to moderate asthma. Ascending doses were tested from 66 mcg once daily to 132 mcg three times daily in a approximately ten volunteers. The study findings demonstrated no clinically significant changes in pulmonary function or reports of pulmonary adverse events.

The API formulations or compositions with the discovered crystal forms may be prepared in various forms for administration, including powders, pellets, tablets, caplets, pills or dragees, or can be filled in suitable containers, such as capsules, blisters or, in the case of suspensions, filled into bottles or vials. Methods of administration of such formulations are well known to those skilled in the art, and include but are not limited to delivery via facemask nebulizers, facemask inhalers, inhalers, nebulizers and variations thereof.

Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers or excipients for medicaments may all be suitable as carrier media.

Preferably the API crystal forms can be prepared for pulmonary or nasal drug delivery using different respiratory formulations with pharmaceutically acceptable excipients such as lactose in its amorphous and crystalline forms and/or dispersed in suitable excipient media matrix as nanoparticles to enable more efficient drug delivery.

In the pharmaceutical compositions of the invention, the active agent may be present in any therapeutically effective amount, which is typically at least 0.1% and generally not more than 90% by weight, based on the total weight of the composition, including carrier medium and/or supplemental active agent(s), if any. Preferably, the proportion of active agent varies between 1-50% by weight of the composition. Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

An appropriate dosage level will generally be about 0.001 to 1000 mg per kg patient body weight per day and can be administered in single or multiple doses. In various aspects, the dosage level will be about 0.01 to about 500 mg/kg per day, about 0.1 to 250 mg/kg per day, or about 0.05 to 100 mg/kg per day. A suitable dosage level can be about 0.001 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For inhalant administration, the compositions are provided in a micronized or inhalant composition containing 0.01 to 1000 milligrams of the active ingredient, particularly 0.01, 0.1 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The polymorph can be administered on a regimen of 1 to 4 times per day, such as once or twice per day. This dosing regimen can be adjusted to provide the optimal therapeutic response.

Unit doses can be administered more than once a day, for example, 2, 3, 4, 5 or 6 times a day. In various aspects, such unit doses can be administered 1 or 2 times per day, so that the total dosage for a 70 kg adult human is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular subject will depend on a variety of factors including the activity of the specific polymorph employed; the age, body weight, general health, sex and diet of the individual being treated; the time and route of administration; the rate of excretion; other drugs that have previously been administered; and the severity of the particular disease undergoing therapy, as is well understood by those of skill in the area.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present invention is further directed to a method for the manufacture of a medicament for treating disease relating to infection by paramyxovirus in animals, including humans comprising combining one or more disclosed polymorphs, products, or compositions with a pharmaceutically acceptable carrier or diluent. Thus, in one aspect, the invention relates to a method for manufacturing a medicament comprising combining at least one disclosed polymorph or at least one disclosed product with a pharmaceutically acceptable carrier or diluent.

The disclosed pharmaceutical compositions can further comprise other therapeutically active polymorphs, which are usually applied in the treatment of the above-mentioned pathological conditions.

In one aspect, the invention relates to pharmaceutical compositions comprising the disclosed polymorphs. That is, a pharmaceutical composition can be provided comprising a therapeutically effective amount of at least one disclosed polymorph or at least one product of a disclosed method and a pharmaceutically acceptable carrier.

In certain aspects, the disclosed pharmaceutical compositions comprise the disclosed polymorphs as an active ingredient, a pharmaceutically acceptable carrier, and, optionally, other therapeutic ingredients or adjuvants. The instant compositions include those suitable for oral, inhaled, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the invention also relates to a pharmaceutical composition comprising a pharmaceutically acceptable carrier or diluent and, as active ingredient, a therapeutically effective amount of a disclosed polymorph, a product of a disclosed method of making, solvate, or a hydrate thereof. In a further aspect, a disclosed polymorph, a product of a disclosed method of making, solvate, hydrate thereof, may be formulated into various pharmaceutical forms for administration purposes.

In practice, the polymorphs of this invention can be combined as the active ingredient in intimate admixture with a pharmaceutical carrier according to conventional pharmaceutical compounding techniques. The carrier can take a wide variety of forms depending on the form of preparation desired for administration, e.g., oral, inhaled or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as particles, as a solution, as a suspension in an aqueous liquid, as a non-aqueous liquid, as an oil-in-water emulsion or as a water-in-oil liquid emulsion. The compositions may be formulated for administration via inhalant methods and devices. In addition to the common dosage forms set out above, the polymorphs of the invention, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions, metered inhalants, or suspensions and the like, and segregated multiples thereof.

Thus, the pharmaceutical compositions of this invention can include a pharmaceutically acceptable carrier and a polymorph as disclosed herein. The polymorphs of the invention can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. It should be emphasized that the above-described embodiments of the present device and process, particularly, and "preferred" embodiments, are merely possible examples of implementations and merely set forth for a clear understanding of the principles of the disclosure. All these and other such modifications and variations are intended to be included herein within the scope of this disclosure and protected by the following claims. Therefore the scope of the disclosure is not intended to be limited except as indicated in the appended claims.

The following specific examples will illustrate the invention as it applies to the methods of treatment using inhalers. It will be appreciated that other examples, including minor variations in procedures will be apparent to those skilled in the art, and that the invention is not limited to these specific illustrated Examples.

EXAMPLES

Crystallization Process Development of P-2 and P-3 Crystal Forms

General

Experiments were carried out to define the crystallization space (in particular, solvent composition and cooling rate) and proved that most important process-relevant crystal forms P-2 hydrate, P-3 ethanolate and P-3 dihydrate can be produced in a controllable fashion.

Example 1

P-3 recrystallization/purification (example of a pilot batch): 540 mg of MDT-637 (starting P-3 ethanolate material with purity approximately 96.5%), was suspended in 13.5 mL of hot acetone at 55±5° C. The resulting mixture was diluted with water (4.4 mL) at 55±5° C. resulting in a clear solution. The solution was added slowly to 18 mL of absolute ethanol with continuous stirring. The clear solution was allowed to stir while cooling naturally to room temperature and stirred for approximately 3 hours. Nucleation was slow, but a heavy precipitate formed during the course of the room temperature stir. The solids were collected by filtration and washed on the funnel with absolute ethanol (3×1 mL). The collected product vacuum dried at 55±5° C. affording 400 mg (74%), HPLC: (99.3 A %), DSC: (onset 256.58° C./peak 262.70° C.), $^1$H NMR: Consistent with structure with residual ethanol. PXRD: form P-3 ethanolate obtained. Product was washed with water and showed conversion into P-3 dihydrate according to the Karl Fischer (KF) analysis (6.8%) and absence of ethanol by $^1$H NMR.

Example 2

P-2 hydrate (recrystallization/purification, demo batch): MDT-637 70.5 g (starting P-3 ethanolate material with purity approximately 96.5%) was suspended in 1,763 mL of acetone at 55±5° C. The mixture was diluted with water (571 mL) while maintaining the temperature at 55±5° C. during the addition. The resulting mixture was allowed to stir at 55±5° C. for approximately 15 minutes. The heat was removed and the mixture cooled naturally to room temperature and stirred overnight. The precipitated solids collected by filtration and washed on the funnel with a 1:1 mixture of acetone/water (3×150 mL). The collected solids vacuum dried at 55±5° C. affording 55.7 grams (79%) product. $^1$H NMR: consistent with structure P-2 with no evidence of residual ethanol or acetone, HPLC: (99.4 A %), KF: (1.2%).

Example 3

Definition of the crystallization space for P-3 ethanolate crystal form (a): Starting P-3 pattern ethanolate was re-crystallized from aqueous-acetone/ethanol (original volume of ethanol used/aq-acetone (0.82v EtOH:1v aq-acetone). Equilibrate at room temperature (R.T). for 24 hours. Cool to 0-5° C. for at least 8 hrs. Material with pattern P-3 was obtained.

Example 4

Definition of the crystallization space for P-3 ethanolate crystal form ce (b): Starting P-3 pattern ethanolate was re-crystallized from aqueous-acetone/ethanol (20% excess ethanol compared to Example 3). (1.15 v EtOH:1 v aq-acetone). Equilibrate at R.T. for 24 hours. Cool to 0-5° C. for at least 8 hrs. Material with pattern P-3 was obtained.

Example 5

Definition of the crystallization space for P-3 ethanolate crystal form (c): Starting P-3 pattern ethanolate was re-crystallized from aqueous-acetone/ethanol (20% less ethanol than in Example 3). (0.5 v EtOH:1 v aq-acetone). Equilibrate at R.T. for 24 hours. Cool to 0-5° C. for at least 8 hrs. Material with pattern P-3 was obtained.

Example 6

Definition of the crystallization space for P-3 ethanolate crystal form (d): Starting P-3 pattern ethanolate was re-crystallized from aqueous-acetone/ethanol/water: (1 v aqueous-acetone:1.7 v (1:1 ethanol/water). Equilibrate at R.T. for 24 hours. Cool to 0-5° C. for at least 8 hrs. Material with pattern P-2 anhydrous form was obtained.

Example 7

Definition of the crystallization space for P-3 ethanolate crystal form (e): Starting P-3 pattern ethanolate was re-crystallized from aqueous-acetone/ethanol (original volume of ethanol used/aq-acetone (0.82 v EtOH:1 v aq-acetone). The hot aq-acetone solution will be added to cold (0-5° C.) ethanol and the resulting mixture further cooled to 0-5° C. and equilibrated at 0-5° C. for approximately 8 hours. Partially amorphous material with pattern P-3 (low crystallinity) was obtained.

Example 8

Definition of the crystallization space for P-3 ethanolate crystal form (f): Starting P-3 pattern ethanolate was re-crystallized from aqueous-acetone/ethanol (original volume of ethanol used/aq-acetone (0.82 v EtOH:1 v aq-acetone). The hot aq-acetone solution will be added to hot (55±5° C.) ethanol and the resulting mixture slowly cooled to 0-5° C. at a rate of ~0.2° C./min. and equilibrated at 0-5° C. for approximately 8 hours. Material with pattern P-3 was obtained. Thus the Examples 1-8 show that production of P-3 pattern ethanolate can be controlled with sufficient amount of ethanol antisolvent (down to 33% v/v ethanol). However excess of water (Example 6) led to P-2 material crystallized. Also very rapid cooling crystallization may lead to low crystallinity product (Example 7).

Example 9

Equilibrium solubility of different API forms in aqueous ethanol: This solubility was determined for P-2 and P-3 crystal forms using slurry equilibration and solution concentration measurement with HPLC. The following solubilities are observed at room temperature in 75/25% v/v ethanol/water: P-3 ethanolate: 239.9 µg/mL; P-2 hydrate: 416.5 µg/mL. These data indicate that P-3 ethanolate is least soluble, and therefore more stable form than P-2 in ethanol/water mixture, As a result, reproducible crystallization process for P-3 ethanolate can be achieved using a thermodynamically-controlled crystallization process.

Example 10

Precipitation of P-2 dihydrate from NMP solution: 594.7 mg of API was dissolved in 20 mL of NMP solvent by stirring and slow heating to 60° C. The resulting stock solution was added to 300 mL pure water and left for 14 hours. The precipitate was washed with water and dried at 40° C. 418 mg of product was obtained which showed to be a partially amorphous P-2 dihydrate form by PXRD analysis.

Example 11

Precipitation of P-2 anhydrous from DMF solution: 8% w/v of API in DMF solution was prepared by stirring and slow heating to 60° C. 5 mL of this stock solution was added to 170 mL methanol antisolvent. Slow precipitation was observed for 2 hours. The precipitate was washed with methanol and dried at 40° C. 260 mg of product was obtained which exhibited the structure consistent with P-2 anhydrous form by PXRD analysis.

Precipitation of Other Forms and Compositions

Example 12

Precipitation of P-4 material DMF solution: 300 mg of API was dissolved in 5 mL of DMF solvent by stirring and slow heating to 60° C. The resulting stock solution was placed in 50 mL open beaker to slowly evaporate for 4 days at room temperature. The precipitate (166 mg) was collected and analyzed using PXRD. The product was identified with P-4 pattern and consisted presumably a DMF solvate form because this pattern was only repeated during evaporation, cooling or antisolvent precipitation with DMF.

Example 13

Precipitation of P-6 material from DMF solution: 5 mL of the 8% w/v API stock solution in DMF was added to 75 mL of MTBE antisolvent. Fast precipitation was observed. The precipitate was washed with MTBE and dried at 40° C. 264 mg of product was obtained which exhibited the structure identified with P-6 pattern by PXRD analysis.

Example 14

Precipitation of P-7 material: 10 mL of 4% w/v API stock solution in NMP was added to 75 mL of cyclohexane. No precipitation was observed for several hours and solvent phase separation occurred. Consequently, 100 ml of water was added and the ternary mixture was stirred for 20 minutes and left to equilibrate for 14 hours. The precipitate was washed with water and dried at 40° C. 380 mg of product was obtained which exhibited the structure identified with P-7 pattern by PXRD analysis.

Example 15

Precipitation of P-8 material: 5 mL of 8% w/v API stock solution in DMSO was added to 100 mL of water. Fast precipitation was observed. The precipitate was washed with water and dried at 40° C. 308 mg of product was obtained which exhibited the structure identified with P-8 pattern by PXRD analysis.

Example 16

Precipitation of amorphous material: 100 mg of API was suspended in 3 mL of hot acetone at 55±5° C. The resulting mixture was diluted with water (0.7 mL) at 55±5° C. resulting in a clear solution. The solution was cast on a glass plate heated at 60° C. 60 mg of the product obtained exhibited no distinct diffraction peaks when analyzed with PXRD and was identified with amorphous structure.

Example 17

Co-precipitation of API with excipient: 100 mg of API was suspended in 13.5 mL of hot acetone at 55±5° C. The resulting mixture was diluted with water (4.4 mL) at 55±5° C. resulting in a clear solution. 500 mg of hydroxypropyl methylcellulose acetate succinate (HPMCAS) was dissolved in the same solution. The solution was cast on a glass plate heated at 60° C. 420 mg of the product obtained exhibited no distinct API diffraction peaks when analyzed with PXRD and was identified with amorphous dispersion of API in the HPMCAS polymer matrix.

Equilibrium Solubility and Thermodynamic Stability of P2 and P-3 Crystal Forms

Example 18

FIG. 23 shows the results of solubility study of drug concentration in stirred suspensions at 25° C. as a function of time for P-2, P-3 forms and their mixture in acetonitrile-water 50/50 v/v solution. It indicates about 40% lower solubility of P-2 compared to P-3 at 25° C. A mixture of forms: P-3 (approximately 75% w/w) and P-2 (approximately 25% w/w), has shown an intermittent solubility. As a function of time, there was a clear reduction of solubility for both P-3 and P-3+P-2 materials. These data indicate lower solubility, greater thermodynamic stability of P-2 and conversion of P-3 form into a less soluble P-2 form at a given temperature.

Example 19

Competitive slurry stability studies over 10 days between P-2 and P-3 crystal forms in 50/50 acetonitrile/water mixture at 25° C. showed that P-3 converts to P-2 as determined using PXRD quantitative phase analysis (based on assessment of multiple peaks ratio). The composition of slurry for P-2 hydrate changed from 50% (day 0) to 77% (4 days) to 85% (10 days). Correspondent solubilities in this solvent system were found to be 190 µg/mL (P-2) and 310 µg/mL (P-3). Therefore P-2 hydrate is more thermodynamically stable at given temperature.

Example 20

An equal powder mixture of six known phases (P-2, P-3, P-4, P-6, P-7 and P-8), 50 mg each were stirred in 75/25 acetone-water solvent (50 mL) at 25° C. over 12 days. PXRD analysis showed that all forms converted convert to P-2 hydrate, which is shown to be the most thermodynamically stable form at these conditions.

Example 21

Simulated lung fluid was prepared according to a method described by Moss et al. (Health Physics 1979, v36, 447-448). The composition of simulated lung fluid (pH 7.4) is showed in TABLE 12.

TABLE 12

| Chemical | | Concentration (g/L) |
|---|---|---|
| Magnesium chloride | $MgCl_2 \cdot 6H_2O$ | 0.2033 |
| Sodium chloride | NaCl | 0.0193 |
| Potassium chloride | KCl | 0.2982 |
| Sodium hydrogen phosphate | $Na_2HPO_4 \cdot 12H_2O$ | 0.3582 |
| Sodium sulphate | $Na_2SO_4$ | 0.0710 |
| Calcium chloride | $CaCl_2 \cdot 2H_2O$ | 0.3676 |
| Sodium acetate | $CH_3COONa \cdot 3H_2O$ | 0.0526 |
| Sodium bicarbonate | $NaHCO_3$ | 2.6043 |
| Sodium citrate | $Na_3H_5C_6O_7 \cdot 2H_2O$ | 0.0970 |

A 0.1% DPPC in water solution was prepared according to a procedure published by Marques et al. (Dissolution Technologies, August 2011). The SLF solution modified with 0.02% DPPC was prepared by diluting the 0.1% DPPC solution with SLF. Refer to NB1181P59-60 for the details on the preparation procedure of SLF and SLF modified with 0.02% DPPC. Two types of DPPC were used in the study. The hydrogenated DPPC was supplied by Lipoid LLC (USA), while the non-hydrogenated DPPC was supplied by Sigma-Aldrich (catalogue # P0763-1G). SLF modified with 0.02% DPPC appeared to be a cloudy/milky suspension, which indicated the formation of micelles and/or emulsions. In order to segregate the solid drug substance from the cloudy solution, a dialysis tube (Sigma-Aldrich catalogue # D9277-100FT) was used. A saturated solution of the drug substance in SLF modified with 0.02% DPPC was prepared and carefully transferred into the dialysis tube (~10 mL in volume). The tube was then put in a container filled with about 100 mL of SLF modified with 0.02% hydrogenated DPPC or 0.02% DPPC. A working bottle was used as the container in the study for SLF with 0.02% hydrogenated DPPC. However, it was determined later that the dialysis tube had better lay-out in a crystallization dish with less turns/kinks. Therefore, a crystallization dish was used as the container in the study of SLF with 0.02% DPPC. For each lot of the drug substance, three samples were set up and placed into a glove box (supplied by Coy Labs) maintained at 37° C. The samples were put on a rotator, which was turned on afterwards at relatively low speed. Samples were taken at different time points for HPLC analysis. A sample preparation procedure for HPLC analysis was developed for samples in SLF modified with 0.02% hydrogenated DPPC or 0.02% DPPC. The sample solution was diluted by 1:3 ratio with ethanol. About one hour after the dilution, it was filtered for HPLC analysis. Glass volumetric pipettes were used and the problem was resolved. The results are shown in FIG. 18.

Chemical and Formulation Stability

Example 22

Forced degradation experiments consisted of placing solid samples of P-2 hydrate and P-3 dihydrate materials in sealed glass bottles at 120° C. for 7 days. The following results were obtained: (a) P-3 sample: API decreased from 98.7% to 93.3%; 6 peaks in control to 16 peaks in stressed sample. (b) P-2 sample: MDT-637 decreased from 99.2% to 99.1%; 4 peaks in control to 5 peaks in stressed sample. The data are shown in TABLE 13. Batche P224-135-2 corresponds to P-2 hydrate and 224-163-1 corresponds to P-3 dihydrate. Thus P-2 form showed to be a more stable form against accelerated solid-state chemical degradation than P-3 dihydrate.

TABLE 13

| | Impurity/Degradation Product | | | | | | | | | | |
|---|---|---|---|---|---|---|---|---|---|---|---|
| | A | B | C | D | E | F | G | H | MDT-637 | I | J |
| RT (minutes) | 1.18 | 2.08 | 2.79 | 3.16 | 9.29 | 10.51 | 12.23 | 13.79 | 16.05 | 17.44 | 18.71 |
| Relative RT | 0.07 | 0.13 | 0.17 | 0.20 | 0.58 | 0.66 | 0.76 | 0.86 | NA | 1.09 | 1.17 |
| Sample Name | | | | | Area % | | | | | | |
| P224-163-1 CTRL | 0.09 | — | — | — | — | — | — | 0.54 | 98.70 | 0.24 | 0.05 |
| P224-163-1 120 C./7 D | 0.12 | 3.60 | 0.17 | 0.48 | 0.25 | 0.08 | 0.05 | 0.43 | 93.32 | 0.17 | — |
| P224-135-2 CTRL | 0.06 | — | — | — | — | — | — | 0.36 | 99.22 | 0.09 | — |
| P224-135-2 120 C./7 D | 0.07 | — | — | — | — | — | — | 0.40 | 99.07 | 0.07 | — |

TABLE 13-continued

| | Impurity/Degradation Product | | | | | | | Total | Grand |
|---|---|---|---|---|---|---|---|---|---|
| | K | L | M | N | O | P | Q | Imp/Deg | Total |
| RT (minutes) | 19.11 | 20.07 | 20.93 | 21.35 | 22.84 | 23.68 | 26.02 | NA | NA |
| Relative RT | 1.19 | 1.25 | 1.30 | 1.33 | 1.42 | 1.48 | 1.62 | NA | NA |
| Sample Name | Area % | | | | | | | | |
| P224-163-1 CTRL | 0.16 | 0.08 | — | — | — | — | — | 1.16 | 99.9 |
| P224-163-1 120 C./7 D | 0.13 | 0.06 | 0.09 | 0.07 | 0.37 | 0.36 | 0.06 | 6.49 | 99.8 |
| P224-135-2 CTRL | 0.16 | — | — | — | — | — | — | 0.67 | 99.9 |
| P224-135-2 120 C./7 D | 0.16 | — | — | — | — | 0.06 | — | 0.76 | 99.8 |

Example 23

The micronized, P-3 dihydrate material was stored in 1.85 mL amber bottles with Teflon lined caps. The 25° C./60% RH and 40° C./75% RH simulated storage and worst-case storage conditions correspondingly. Data through 12 months for API storage in glass bottles indicated that no change in form was observed according to both DSC and PXRD analyses.

Example 24

P-3 dihydrate and P-2 hydrate materials were placed in open wide glass bottles at 40° C./75% RH for 4 weeks. The results indicated no change of form by both DSC and PXRD analyses. Acceptable chemical stability was observed for both forms as shown in TABLE 14.

TABLE 14

| Attribute | P-2 | P-3 |
|---|---|---|
| Assay | 98.8% | 96.7% |
| Rel Subs | 0.68% | 0.67% |
| Water | 3.5% | 5.9% |

Example 25

Formulation of the P-3 dihydrate form of the API with lactose (6.3% w/w) was placed on stability 40° C./75% RH in sealed glass bottles for 39 weeks. After samples removal, the lactose was removed by dissolution in purified water. The reference formulation was also subjected to the same lactose extraction procedure to eliminate the possibility for form conversion in water. The stability samples indicated no change of crystal form.

Micronization and Formulation

Example 26

Four lots of MDT-637 API were micronized using a 2-inch spiral jet mill. The approximate amounts of material available from each of the experiments and the initial particle size distributions (PSDs) of the unmilled materials are list in Table 15.

TABLE 15

| Lot | Quantity (g) | $X_{10}$ (µm)* | $X_{50}$ (µm)* | $X_{90}$ (µm)* | XRPD Pattern |
|---|---|---|---|---|---|
| P218-75-4 | 50 | 0.81 | 2.77 | 16.37 | P-3/P-2 (predominantly P-3) |
| P224-135-2 | 50 | 1.28 | 10.35 | 77.40 | P-2 |
| P224-131-2 | 50 | 1.36 | 10.61 | 78.99 | P-2 |
| P224-177-1 | 6 | 0.92 | 3.67 | 19.89 | P-3 |

The resulting particle size distribution (PSD) percentiles are shown in TABLE 16 for micronized P-2 hydrate, P-3 dihydrate and a physical mixture materials.

TABLE 16

| Lot | | $X_{10}$ (µm) | $X_{50}$ (µm) | $X_{90}$ (µm) | Sample Number | Milling Pressure (psi) |
|---|---|---|---|---|---|---|
| P218-75-4 | First Pass, 50 g | 0.49 | 1.16 | 2.45 | I-1 | 120 |
| | Second Pass, 25 g | 0.47 | 1.10 | 2.20 | I-2 | 120 |
| P224-135-2 | 25 g (initial) | 0.59 | 1.67 | 4.62 | I-3 | 80 |
| | 25 g (final) | 0.60 | 1.73 | 5.29 | I-4 | 80 |
| P224-131-2 | 25 g (initial), First Pass | 0.65 | 1.96 | 5.58 | I-5 | 80 |
| | 25 g (initial), Second Pass | 0.62 | 1.77 | 5.16 | I-7, re-pass | 20 |
| | 25 g (final) | 0.62 | 1.80 | 5.08 | I-6 | 110 |
| P224-177-1 | 1 pass | 0.53 | 1.19 | 2.49 | I-8 | 80 |

It was noticed that at higher milling pressure the P-2 hydrate material yielded larger particles compared to P-3 dihydrate material which was attributed to higher hardness of the P-2 hydrate compound as both materials show a similar acicular particle shape. Micronization of both forms could be sufficiently controlled to produce PSD in a desired respiratory size range (e.g. $D_{50}$ between 1-2 µm and $D_{90}$<5 µm). In addition, micronization did not affect the crystallinity, phase purity of both P-3 dihydrate and P-2 hydrate forms.

Example 27

Safety and Tolerability of MDT-637 P3

The purpose of the following studies was to assess the safety, tolerability, local and systemic pharmacokinetics of single and multiple doses of MDT-637 P3 in healthy volunteers and asthmatics.

For Phase 1 studies, an inhaler such as the MicroDose Inhaler (an active, electronic DPI) was developed to synchronize drug aerosolization with adult tidal breathing, and adapted to fit a valved aerosol mask (FIG. 24). In summary, the MicroDose Inhaler operation comprises the drug powder contained in a protective blister until delivery. The blister is pierced externally and then placed in contact with a piezoelectric vibrator within the MicroDose Inhaler. When the patient inhales, an airflow sensor automatically turns on the piezo which provides energy to deaggregate the particles of powder and aerosolizes them into the inhalation airstream, providing synchronized delivery. The MicroDose Inhaler was triggered by pressure drop and programmed to produce a series of brief aerosol bursts of predetermined duration within the range of 0.1 to 2.0 seconds, preferably 0.1 seconds, early during each inhalation cycle and for 16 consecutive breaths. The studies were conducted as follows:

Study 1: A Randomized, Double-blind, Placebo-controlled, Single Ascending Dose (SAD) Study to Assess the Safety, Tolerability and Pharmacokinetics of Inhaled MDT-637 in Healthy Volunteers (SAD Trial)

Study Objective: The objective of Study 1 was to determine the range of inhaled doses of MDT-637 P3 that are safe and well-tolerated including effects on "Forced Expiratory Volume in the First Second" ($FEV_1$). An additional objective was to determine the rate and extent of systemic absorption of MDT-637 P3 and trough nasal wash MDT-637 P3 drug concentrations after a nasal inhalation.

Study Design: Single-center, double-blind, randomized, placebo-controlled, sequential group.

Each subject received (Once Daily or Three Times Daily (TID) over a single day) nasally inhaled dose(s) of MDT-637 P3 (or placebo) listed below. The study consisted of 3 visits: Visit 1 (Screening), Visit 2 (Dosing) and Visit 3 (Follow up); subjects furloughed from the clinic between Visits 2 and 3. Subjects who met all of the inclusion criteria and who meet none of the exclusion criteria (Table 17, FIG. 27) at Visit 1 were eligible to return for Visit 2 within 14 days of screening. The subject was admitted to the study center the day prior to dosing, was observed at the study center for at least 24 hours after dosing, and returned for Visit 3, 7 days after dosing.

Groups of 8 subjects were enrolled into each of the following cohorts randomized 3:1 (active:placebo):

| Treatment Cohort | Treatment (expressed as target emitted dose exiting the facemask) |
|---|---|
| 1 | MDT-637, 8 mcg Once Daily or placebo |
| 2 | MDT-637, 33 mcg Once Daily or placebo |
| 3 | MDT-637, 33 mcg TID or placebo |
| 4 | MDT-637, 66 mcg Once Daily or placebo |
| 5 | MDT-637, 66 mcg TID or placebo |
| 6 | MDT-637, 132 mcg 3 times daily or placebo |

Study Drug and Formulation

Placebo: Inhalation grade lactose blend (100% RESPITOSE® ML003 (Princeton, N.J., USA))

Active: Micronized MDT-637 P3 formulated $^{w/w}$ as a dry powder with inhalation grade lactose (ML003)

Low strength formulation: 0.63% $^{w/w}$ MDT-637 in RESPITOSE® ML003 High strength formulation: 6.3% $^{w/w}$ MDT-637 in RESPITOSE® ML003 Dose and Route of Administration The doses of MDT-637 P3 were determined based on the no adverse effect level (NOAEL) in GLP toxicology studies in two species, as well as on the basis of previous clinical experience with a previous inhaled solution formulation (referred to as VP14637 Drug Product). Both active and matched placebo were administered via face mask inhalation from a proprietary delivery system (MicroDose inhaler).

At each dose level, 6 subjects received MDT-637 P3 and 2 subjects received matched placebo. Based on safety and tolerability results from each cohort, the Principal Investigator, Medical Monitor and MDT jointly decided whether to proceed to the next dose level based upon protocol-specified dose escalation rules. At least 7 days (between Visit 2 dosing days in subsequent dose groups) separated successive dosing cohorts. A second cohort was available to be studied at any dose level if needed to confirm findings from the initial cohort at that dose.

Single doses were administered in the morning. TID doses will be administered at 6 hour intervals, with the 1st of the 3 doses administered in the morning.

Assessments

Primary Endpoints

Safety and tolerability, were assessed by:

Vital signs at Visits 1, 2 and 3

Physical examination at Visit 1, 2 and 3

Routine laboratory tests (hematology, clinical chemistry, urinalysis) at Visit 1 (screening), Visit 2 and Visit 3 (discharge)

ECG at Visits 1, 2 and 3

Spirometry (FEV1) assessed at Visit 1 (screening) and Visit 2 i.e., comparing pre and post dosing Adverse event assessment from administration of study drug until subjects were discharged from the study Secondary Endpoints Pharmacokinetic endpoints (Cmax, Tmax, AUC, T1/2) and dose proportionality were assessed based on a limited number of plasma samples from Visit 2

Analysis

Demographic and baseline information was presented and summarized by treatment sequence and across the entire group. Subjects who were enrolled in the study and received study treatment could have been replaced (at the discretion of the Sponsor) if they discontinued prior to the completion of the study. Subjects were not replaced if they were discontinued from the study secondary to an adverse event/adverse experience (AE) unless the AE could be determined to be unrelated to treatment.

Safety and tolerability were evaluated based on the results of physical examination, electrocardiogram (ECG) (with QTc intervals), laboratory tests (urinalysis, hematology, chemistry), spirometry and adverse event assessments following study drug administration.

Pharmacokinetic variables (Cmax, Tmax, AUC, T1/2) were evaluated based on blood samples drawn at Visit 2.

Study 2: A Randomized, Double-blind, Placebo-controlled Study to Assess the Safety, Tolerability and Pharmacokinetics of Inhaled MDT-637 (P3) Administered to Healthy Volunteers for 10 Days (Multiple Ascending Dose: MAD Trial)

Study Objective: The objective of Study 2 was to assess the tolerability and safety of a range of repeated inhaled doses of MDT-637 P3 that had been developed for patients with RSV infection. A second objective of Study 2 was to determine the rate and extent of systemic absorption of MDT-637 P3 and nasal mucosal MDT-637 P3 drug concentrations across 10 days of dosing.

Study Design: Single-center, double-blind, randomized, placebo-controlled, sequential group.

Subjects were enrolled in cohorts of 12 subjects. Within each cohort, 9 subjects received nasally inhaled dose(s) of MDT-637 P3 and 3 subjects received matching placebo. The study consisted of 3 visits: Visit 1 (Screening), Visit 2 (Dosing), Visit 3 (Follow up) and subjects remained at the study site for pharmacokinetic (PK) sampling, spirometry, and safety assessments. Subjects who met all of the inclusion criteria and who meet none of the exclusion criteria (Table 18, FIG. 28) were eligible for this study. Day 1 was the first day of dosing and Day 10 was the final day of dosing, following which subjects remained at the study site for 24 hours following the last dose for PK sampling and spirometry. Visit 3 was a follow-up visit, 7 to 10 days after the last dose. Cohorts were dosed as follows:

| Treatment Cohort | Treatment (expressed as target emitted dose exiting the facemask) |
|---|---|
| 1 | MDT-637 P3, 66 mcg twice daily (BID) or placebo |
| 2 | MDT-637 P3, 66 mcg three times daily (TID) or placebo |
| 3 | MDT-637 P3, 132 mcg TID or placebo |

Study Drug and Formulation

Placebo: Inhalation grade lactose processed in identical manner to active clinical blend (100% RESPITOSE® ML003)

Active: Micronized MDT-637 P3 formulated at 6.3% $^{w/w}$ as a dry powder with inhalation grade lactose (RESPITOSE® ML003)

Dose and Route of Administration

The doses of MDT-637 were determined based on the NOAEL in GLP toxicology studies, as well as on the basis of previous clinical experience in Study 1 (above). Both active and matched placebo was administered via facemask using a MicroDose inhaler device.

At each dose level, 9 subjects received MDT-637 P3 and 3 subjects received matching placebo. Based on safety and tolerability results from each cohort, the Principal Investigator, Medical Monitor and the Sponsor (MDT) jointly decided whether to proceed to the next dose level based upon protocol-specified dose escalation rules. Dose escalation from Cohort 5 (66 mcg TID) to Cohort 6 in Study 1 was required for the initiation of Cohort 1 in this study. At least 7 days separated the last dose (i.e. Day 10) for a given cohort from the initiation of dosing in the subsequent dosing cohort, following review of all safety data and a decision made to dose escalate. A second cohort may have been studied at any dose level if needed to confirm findings from the initial cohort at that dose.

The first doses for twice daily (BID) and three times daily (TID) were administered in the morning, starting at approximately 0700 hours on each day of dosing. BID doses were administered at 12 hour intervals and TID doses were administered at 6 hour intervals each dose day.

Assessments

Primary Endpoints

Safety and tolerability, was assessed by:

Vital signs (blood pressure, heart rate, temperature and respiratory rate) and pulse oximetry at Visits 2 and 3

Physical examination at Visits 2 and 3

Routine laboratory tests (hematology, clinical chemistry, urinalysis) at Visits 2 and 3

ECG at Visits 2 and 3

Spirometry at Visits 2 and 3

Adverse event assessment from administration of study drug until subjects are discharged from the study Secondary Endpoints Pharmacokinetic endpoints (Cmax, Tmax, AUC, T1/2) and dose proportionality was assessed based on a limited number of plasma samples following the first dose on Day 1 and last dose on Day 10

Trough plasma samples for MDT-637 P3 concentration was obtained within 30 minutes prior to the first daily dose on Days 2, 5 and 10

MDT-637 concentrations determined from nasal wash samples prior to and 15 minutes post dose on Day 6 and 24 hours post last dose (Day 11)

Analysis

Demographic and baseline information was presented and summarized by treatment sequence and across the entire group.

Subjects who were enrolled in the study and received study treatment may have been replaced (at the discretion of the Sponsor) if they discontinued prior to the completion of the study. Subjects were not replaced if they were discontinued from the study secondary to an AE unless the AE was determined to be unrelated to treatment.

Safety and tolerability were evaluated based on the results of physical examination, ECG, laboratory tests (urinalysis, hematology, chemistry), spirometry and adverse event assessments following study drug administration.

Pharmacokinetic variables (Cmax, Tmax, AUC, T1/2) were evaluated based on blood samples drawn following first dose (Days 1-2) and last dose (Days 10-11).

Study 3: A Double-Blind, Randomized, 3 Period Crossover, Single Ascending Dose Study to Assess the Safety and Tolerability of Inhaled MDT-637 P3 in Subjects With Intermittent or Mild-to-Moderate Persistent Asthma (Asthma Trial)

Study Objective: The primary objective of Study 3 was to assess the safety and tolerability of MDT-637 P3 when inhaled by subjects with Intermittent, or Mild-to-Moderate Persistent, Asthma. A secondary objective of Study 3 was to determine the rate and extent of systemic absorption of MDT-637 and trough nasal wash MDT-637 drug concentrations following dry powder inhalation dosing.

Study Design: Single-center, double-blind, randomized, 3 period crossover, ascending dose.

Each subject was dosed on 3 separate days during the study. Each subject received an initial dose of placebo (Period 1), followed by random allocation at Period 2 to a single dose of nasally inhaled MDT-637 P3 or double blind placebo. After an observation and furlough period, subjects returned for Period 3 to receive three doses of study drug (MDT-637 P3 or placebo) over a single day as listed below. The study consisted of 5 visits: Visit 1 (Screening), Visits 2, 3 and 4 (Dosing), and Visit 5 (Follow up); subjects were furloughed from the clinic for 6 up to 14 days between Visits 3 and 4 and 7-8 days between Visit 4 and 5. Subjects who met all of the inclusion criteria and none of the exclusion criteria (Table 19, FIG. 29) at Visit 1 were eligible to return for Visit 2 within 42 days of screening. Subjects were admitted to the study center twice, once for Visit 2 and again for Visit 4. Visit 5, was a safety follow up (outpatient) visit.

A single group of approximately 10 subjects was enrolled into the study.

| Visit | Treatment (expressed as target emitted dose exiting the facemask) |
|---|---|
| 1 | Screening |
| 2 | Placebo |
| 3 | Double-blind, randomized MDT-637, 66 mcg or placebo Once Daily |
| 4 | Double-blind, randomized MDT-637, 132 mcg or placebo TID |
| 5 | Follow-Up visit |

Study Drug and Formulation

Placebo: Inhalation grade lactose processed in an identical manner to active clinical blend (100% RESPITOSE® ML003)

Active: Micronized MDT-637 P3 formulated $^{w/w}$ as a dry powder with inhalation grade lactose (ML003)

Dose and Route of Administration

The doses of MDT-637 P3 were determined based on previous clinical experience in Study 1. Both placebo and active were administered as a dry powder for nasal inhalation via a face mask using a MicroDose Inhaler device. At Visit 2, all 10 patients were dosed with placebo Once Daily. At Visit 3, subjects were randomly allocated so that 8 subjects were dosed with MDT-637 P3 Once Daily 66 mcg and 2 subjects received double blind placebo. At Visit 4, subjects were again randomly allocated so that 8 subjects were dosed with MDT-637 TID 132 mcg and 2 subjects received double blind placebo.

Based on safety and tolerability results from each visit in Study 3 and safety data from Study 1 and Study 2, the Principal Investigator, Medical Monitor and Sponsor (MicroDose Therapeutx, MDTx) could jointly decide whether to proceed to the next dose administration based upon protocol-specified dose escalation rules. At least 7 days (between Visit 3 and Visit 4) separated successive dosing cohorts. A second cohort could have been studied at any dose level if needed to confirm findings at that dose. Single doses were administered in the morning, starting at approximately 0700 hours. TID doses were administered at 6 hr intervals, with the first of the 3 doses administered at approximately the same time in the morning as the Once Daily doses are administered.

Assessments

Primary Endpoints

Safety and tolerability, was assessed by:

Adverse event assessment from administration of study drug until
  discharge from the study
  Vital signs at Visits 2, 3, 4 and 5
  Physical examination at Visits 2, 4 and 5
  Routine laboratory tests (hematology, clinical chemistry, urinalysis) at Visits 2, 3, 4 and 5
  ECG at Visits 2, 3, 4 and 5
  Spirometry ($FEV_1$) at Visit 3 and Visit 4.

Secondary Endpoints

Pharmacokinetic endpoints (Cmax, Tmax, AUC, T1/2) were assessed based on a limited number of plasma samples from Visit 4

Trough MDT-637 P3 concentrations determined from nasal wash

Analysis

Demographic and baseline information was presented and summarized by treatment and across the entire group.

Subjects who were enrolled in the study and received study treatment but withdrew before study completion could have been replaced at the discretion of the Sponsor. Subjects were not replaced if they discontinued from the study secondary to an AE unless the AE could be determined to be unrelated to treatment.

Safety and tolerability were evaluated based on the results of adverse event assessments, physical examination, vital signs, spirometry, ECG (with QTc intervals), and laboratory tests (urinalysis, hematology, chemistry) following study drug administration.

Pharmacokinetic variables (Cmax, Tmax, AUC, T1/2) were evaluated based on blood samples drawn at Visit 4. Nasal trough concentrations at Visit 4 were listed.

Results and Discussion

Study 1: Single Ascending Dose Study
  Ascending doses tested from 2 mcg once daily to 132 mcg three times daily in 35 volunteers
  MDT-637 P3 was safe and well tolerated at doses up to 132 mcg TID
  Overall, 4 subjects (11.4%) reported experiencing 4 TEAEs during the study (No significant changes in pulmonary function or reports of pulmonary AEs)
  Mild dizziness was sole treatment emergent adverse event considered possibly related by PI
  No clinically significant changes in labs, vital signs, ECGs, physical exams
  Nasal wash levels at 24 hours post dose were >MDT-637 P3's $IC_{50}$ for RSV
  Consistent and low PK exposure (Mean $C_{max}$ of 33.7±4.6 picograms/mL (132 mcg TID cohort)

Study 2 Multiple Ascending Dose Study
  Ascending doses tested up to 132 mcg three times daily for 10 days in 38 volunteers
  MDT-637 P3 was safe and well tolerated at doses up to 132 mcg TID for 10 days
  No significant changes in pulmonary function or reports of pulmonary AEs (FIG. 25)
  25 subjects reported no treatment emergent adverse events (TEAEs)
  The remaining 13 subjects reported a total of 20 TEAEs overall, all considered mild
  5 TEAEs were considered related to study treatment: eye twitching (possibly), dry throat (related), headache (possibly, placebo), sore throat (possibly) and lethargy (possibly). No action was taken on any of the events and all reported as 'resolved'
  No clinically significant changes in labs, vital signs, ECGs, physical exams
  Nasal wash levels at pre/post-dose and 24 hours post dose were >MDT-637 P3 $IC_{sci}$ for RSV
  Consistent and low PK exposure (FIG. 26), with minimal accumulation.
  Day 10 mean $C_{max}$ ~50 picograms/mL for 132 mcg TID $AUC_{0-24}$ was 1.16 ng·h/mL)
  CVs in the 15-30% range (excellent consistency)

Study 3: Single Ascending Dose in Asthmatics
  Ascending doses tested from 66 mcg once daily to 132 mcg TID in n=10 subjects to rule out repeat dose irritancy in patients with more sensitive airways
  MDT-637 P3 was safe and well tolerated in asthmatic patients
  No clinically significant changes in pulmonary function or reports of pulmonary AEs
  No clinically significant changes in labs, vital signs, ECGs, physical exams
  8/10 subjects reported no adverse events
  The remaining 2/10 subjects reported (1) unrelated menstrual migraine symptoms during the placebo phase and (2) moderate headache and mild nausea considered possibly related.
  Pharmacokinetics were comparable between the healthy and asthmatic population

CONCLUSIONS

The above Studies demonstrate that MDT-637 P3 is safe and well tolerated in three studies at doses up to 132 mcg TID for 10 days.

MDT-637 P3 exhibited highly consistent and low systemic exposure, which is considered ideal for pediatric dosing. Importantly, no serious adverse events were observed. Nasal levels of MDT-637 P3 quantified 15 min, 6 hr and 24 hr post dose were >RSV $IC_{50}$.

Finally, no pulmonary adverse events or changes in pulmonary function were observed and no clinically significant changes in ECG, laboratory values, vital signs or physical exam were observed either.

It will be appreciated by those skilled in the art that the present invention can be embodied in other specific forms without departing from the spirit and essential characteristics thereof. The presently disclosed embodiments are therefore considered in all respects to be illustrative and not restricted. The scope of the invention is indicated by the appended claims rather than foregoing description and all changes that come within the meaning and range and equivalence thereof are intended to be embraced therein.

What is claimed is:

1. A composition comprising at least one polymorph of MDT-637 selected from the group consisting of amorphous form, P-2 hydrate crystal form, P-3 dihydrate crystal form, P-3 ethanolate crystal form, P-3 monohydrate crystal form, P-3 anhydrous crystal form, P-2 anhydrous crystal form, P-4 crystal form, P-6 crystal form, P-7 crystal form, P-8 crystal form, and combinations thereof.

2. The composition of claim 1, additionally comprising one or more pharmaceutically acceptable carriers.

3. The composition of claim 1, wherein the at least one polymorph of MDT-637 comprises a crystal form of P-2 hydrate.

4. The composition of claim 1, wherein the at least one polymorph of MDT-637 comprises a crystal form of P-3 monohydrate.

5. The composition of claim 1, wherein the at least one polymorph of MDT-637 comprises a crystal form of P-3 dihydrate.

6. The composition of claim 1, wherein the at least one polymorph of MDT-637 comprises a crystal form of P-2 anhydrous.

7. The composition of claim 1, wherein the at least one polymorph of MDT-637 is a crystal form of P-3 anhydrous.

8. The composition of claim 1, wherein the at least one polymorph of MDT-637 is a crystal form of P-3 ethanolate.

9. The composition of claim 1, wherein the at least one polymorph of MDT-637 is selected from P-4 crystal form, P-6 crystal form, P-7 crystal form, or P-8 crystal form.

10. The composition of claim 1, wherein the at least one polymorph of MDT-637 is dispersed in at least one pharmaceutical excipient to provide a solid composite.

11. A method of treating a subject having a disease resulting from infection by Paramyxovirinae or Pneumovirinae, comprising administering to the subject a compound in an amount effective to treat the subject wherein the compound comprises at least one polymorph of MDT-637 selected from the group consisting of amorphous form, P-2 hydrate crystal form, P-3 dihydrate crystal form, P-3 ethanolate crystal form P-3 monohydrate crystal form P-3 anhydrous crystal form P-2 anhydrous crystal form P-4 crystal form P-6 crystal form, P-7 crystal form, P-8 crystal form and combinations thereof.

12. The method of claim 11, wherein the at least one polymorph of MDT-637 is selected from P-2 hydrate crystal form, P-3 monohydrate crystal form and P-3 dihydrate crystal form.

13. The method of claim 11, wherein the method of treating the disease comprises alleviating and preventing symptoms associated with respiratory syncytial virus wherein the symptoms comprise rhinitis, otitis media, pneumonia and bronchiolitis.

14. The method of claim 11, wherein the compound is administered to the subject via inhalation.

15. A method of treating a subject having an infection associated with respiratory syncytial virus, comprising administering to the subject a compound in an amount effective to treat the subject wherein the compound comprises eat least one polymorph of MDT-637 selected from the group consisting of amorphous form P-2 hydrate crystal form P-3 dihydrate crystal form, P-3 ethanolate crystal form, P-3 monohydrate crystal form, P-3 anhydrous crystal form, P-2 anhydrous crystal form, P-4 crystal form, P-6 crystal form, P-7 crystal form P-8 crystal form and combinations thereof.

* * * * *